United States Patent
Hamdan et al.

(10) Patent No.: US 10,443,048 B2
(45) Date of Patent: Oct. 15, 2019

(54) DNA POLYMERASES FROM THE RED SEA BRINE POOL

(71) Applicant: KING ABDULLAH UNIVERSITY OF SCIENCE AND TECHNOLOGY, Thuwal (SA)

(72) Inventors: Samir M. Hamdan, Thuwal (SA); Masateru Takahashi, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 62 days.

(21) Appl. No.: 15/302,986

(22) PCT Filed: Apr. 10, 2015

(86) PCT No.: PCT/IB2015/001423
§ 371 (c)(1),
(2) Date: Oct. 8, 2016

(87) PCT Pub. No.: WO2015/166354
PCT Pub. Date: Nov. 5, 2015

(65) Prior Publication Data
US 2017/0029793 A1    Feb. 2, 2017

Related U.S. Application Data

(60) Provisional application No. 61/978,406, filed on Apr. 11, 2014.

(51) Int. Cl.
*C12N 9/12*    (2006.01)
*C12P 19/34*    (2006.01)

(52) U.S. Cl.
CPC ............ *C12N 9/1252* (2013.01); *C12P 19/34* (2013.01); *C12Y 207/07007* (2013.01)

(58) Field of Classification Search
None
See application file for complete search history.

(56) References Cited

FOREIGN PATENT DOCUMENTS

WO    2007/043769    4/2007
WO    2012/173905    12/2012

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
International Search Report dated Dec. 3, 2015, issued in International Application No. PCT/IB2015/001423.
Written Opinion of the International Searching Authority dated Dec. 3, 2015, issued in International Application No. PCT/IB2015/001423.
International Preliminary Report on Patentability (Chapter I of the Patent Cooperation Treaty) dated Oct. 12, 2016, issued in International Application No. PCT/IB2015/001423.
Takagi M et al: "Characterization of DNA Polymerase from *pyrococcus* Sp. Strain Kod1 and its Application to PCR", Applied and Environmental Microbiology, American Society for Microbiology, US, vol. 63, No. 11, Nov. 1, 1997 (Nov. 1, 1997), pp. 4504-4510, XP002947648, ISSN: 0099-2240 p. 4504, col. 1, paragraph 2-col. 2, paragraph 1 p. 4507; table 2 p. 4508, col. 1, paragraph 2-p. 4509, col. 1, paragraph 3.
Huimin Kong et al: "Characterization of a DNA Polymerase from the Hyperthermophile Archaea Thermococcus Litoralis. Ovent DNA Polymerase, Steady State Kinetics, Thermal Stability, Processivity, Strand Displacement, and Exonuclease Activvities", Journal of Biological Chemistry, American Society for Biochemistry and Molecular Biology, US, vol. 268, No. 3, Jan. 25, 1993 (Jan. 25, 1993), pp. 1965-1975, XP000611227, ISSN: 0021-9258 p. 1965, col. 2, paragraph 2 p. 1968, col. 2, paragraph 6-p. 1969, col. 1, paragraph 1.
Takagi M et al: "Characterization of DNA Polymerase From *pyrococcus* Sp. Strain Kod1 and its Application to PCR", Applied and Environmental Microbiology, American Society for Microbiology, US, vol. 63, No. 11, Nov. 1, 1997 (Nov. 1, 1997), pp. 4504-4510, XP002974648, ISSN: 0099-2240 p. 4504, col. 1, paragraph 2-col. 2, paragraph 1 p. 4507; table 2 p. 4508; col. 1, paragraph 2-p. 4509, col. 1, paragraph 3.
Huimin Kong et al.: "Characterization of a DNA Polymerase from the Hyperthermophile Archaea Thermococcus Litoralis. Ovent DNA Polymerase, Steady State Kinetics, Thermal Stability, Processivity, Strand Displacement, and Exonuclease Activities" Journal of Biology Chemistry, American Society for Biochemistry and Molecular Biology, US, vol. 268, No. 3, Jan. 25, 1993 (Jan. 25, 1993), pp. 1965-1975, XP000611227, ISSN: 0021-9258 p. 1965, col. 2, paragraph 2, p. 1968, col. 2, paragraph 6-p. 1969, col. 1, paragraph 1.

* cited by examiner

*Primary Examiner* — Richard G Hutson
(74) *Attorney, Agent, or Firm* — Pabst Patent Group LLP

(57) ABSTRACT

A DNA polymerase composition for amplifying nucleic acids can be tolerant of extreme conditions.

6 Claims, 12 Drawing Sheets
Specification includes a Sequence Listing.

amino acids sequence alignment

```
              491         500         510              520    525  530
gp5       ----FDNGEYAHEILNGDIHTKNQIAAELPTR--------DNAKTFIYGFLYGAGDEKI
clone3    ALKIIANSFYGMLGYPRARWYSKECAESVTSFGRHYIKDTIEMAKDEGFEVIYGDTDSLF
              : *. *.        .:: *  ,:.:        : **   :  .:** *. :
```

SEQ ID NO:1- Clone1 (BR1)
MRETSEGWLLDAYIEGRYAVLWLKSIDGTVHRLRERYRPCFYAEPRDDCRIEDAASTIETHPAVHSALE
VERYATLRRREVKRVVKVSVESTDELDQAVAFARRHQMVRELYNVGLTPVQWYLFQLDAAPSSHVE
WTRRGGVLESITVLDGGLRVEPPPFKPHQTSKPPIEEVDLYDDCGSHLAALRGCEREVLSELQGAVTEI
DPDIVAMVDGVDTIRRLRQRAGAKGVDLCVGRLGDASHGRVALENRWFRDLGVVGLVERARFAMAP
MGVCAGWAAGRTVDSRQCYEADRLGVLVSEMKGGYAYAATAWELLFRDRGGMVLSPEMGLHENV
GVLDFESMYPNHVTRNVSYENITPNGVERGPQGFLGGFTRRFLRRRLHYKHLRSSYPTDSREWRWCEQ
RQRSLKLMLVVIYGYSGCYANRFGNVRVFQEINRVARQALVESLNTALSRGYRVVYGDSDSLFTAKQ
GATREDYLGLAEEIAEATGLPITLDRHFKYLVLLPQAGDPEMGAARRYYGKLTDGTLFYRGIELRRRDT
PPYIRRLQRRVMETLFNADTAEEVRGRQLPKALELVKAACAELLRGQVDPRELVVSKRLRRRPGDYAS
KQPHVVAAQLEGLEEGYSEFLYVNSERRNPYIRVMPASMVNGGHHTIDRAWYSSMARRAAENILRPFL
DEGSNGGGKLRVSRLDTFFSRR

SEQ ID NO:2 - Clone2 (BR2)
MKAYLLDIDYTTVKDRAEVKLYLRGEEGRLEVYDRNFLPYFYVLGDEVEEKLLEEGALKVEGRRKKL
LGREVKALQVFASHPQEVPELRNKVKKIEGVDLTLEDDILFTRRYLIDRGMKPLTWYDFDVREEGGKY
YLQGFKEIEGGSPGLRTVALDIEVYNPGGVPRPEEDPHMVSLAGSGGLKKVLTWKDEGEVPGFVEVLS
SEGAMLGRLEEIFKEEEIDVVVGYNTDNPDFPYIKKRLQTLDMELQLGGDNIKIKGRKSLPQAALGGLP
HLDLYPIVRRNVRLNSYVLENVLKEVLKEEKEKIPNEKIWEYWDAGGEKLEKLFHYSLEDAEGTLRLS
QRFVPLYVQLSAIVGQCLYDTSRMTTGQMVEWYLMRIASRASELIPNRPKGEELKGRFSTTYAGGYVH
QPRKGMVRDIAVFDFRSLYPSHVTHNIDPSTLREGVGCEENKAPSLDYCFSREEKGFIPSILEGLVNWRG
EVKKKMEGKGGEELRTLDFTQKALKILSNSPYGYMGYPRARWYRRECAESVASFAREYIKKVMATAK
EEFGLEVVYGDTDSLFVLLPGKEKARAEEFLEHVNRSMPGHQLELEGFYLRGLFVSKKRYALLDEKGK
ITVKGLEFVRRDWAPIARETQQKVLEILLKEGDEGKALRLVREVIENIKRREVTLNQISIYTQLTRKVES
YEGKEPHVGAAKKLQDEGYKVKAGSHGYIVAKGRKGEKISERTLPVELASVEDYDPNYYIENQILPAV
GRIPDALGYRRDYIKTGVEQRSLGKWIS

SEQ ID NO:3 - Clone3 (BR3)
MANQTTNGDHMEGLLLDSDYLKTRKPPAMRLFIKKDGGIVTVLDPHFTHYFYVESENPQKIAKAIERV
EAEKYGKKVSPKSTKVVERKPLGEEKKVIKVLADSPRDITPLRKEIKDFPEVKGFYEHDIPPARRYLIEH
ELTPMSGVKAEGESQKGDYGEELVLTKPPESIEGADEELNILAFDIETYSPTGNPRAEKDPIVMISVSDN
QGLEKILTWKDFDLNLDYVEVLDDEKSMIERFIQLVQECDADIIMGYNTDLFDFPYLTQRAEKLDIKLE
LGRDGSEPSTKKRRFEATVTKIAGRVHADVYAMVEFLSRIGAIRLIDYTLENVYKHVIGKEKPDLEYSDIP
KAWDEGGEKARELVEYSLSDAKATLELGTEILPLFTELSRTVKQSLFDVSRMTPGQLVEWLLIFNAHKF
NELILPRPLGREYKRRRGETYIGGYVKEPTPGLHEDLVVFDFRSLYPTHITHNIDPATLDGERCPSEETVT
APDLEYEFCQDRKGFIPETLKGLVEGRAKLKQEMSQLDEESREYQSLYNRQWALKHANSPYGMLGYP
RARWYSKECAESVTSFGRHYIKDTHEMAKDEGFEVIYGDTDSLFAKLNGKSREDVENFLNKVNESLPGI
MKLELEDYYKRGVFVTKKRYAMISEDDKIVVKGLEFVRRDWAALAKRTQEQVIEAILHDASPEKAAKI
VLETTKAIKQGEVDLDDLVIHTQLKKPLDEYKARGPHVAAAERLQKLGEEVEPGMTITYIVEKGSGSIS
DRAIPPSDFEGRDYDPDYYVENQVLPAVMRIMEVLDYGEEDLRHEETRQVKLGKFK

SEQ ID NO:4 - Clone6 (BR6)
MEEKIYLLDLDYIEEETERGMEATVRLWGKNGEGKSVVAWDRAFDPYFYYVPGDFPLAKERLEGVDE
PRIKGVEEAEKILGKEEVKALRVYGSRPSDLPKLRDKLKGEGFDGERFYEYGMSFYRQYVVSKGLLPA
SWVLVKGKEVEKEGFDLAFEAGEVQALEGEEEAPLKTLAFDLETYESQEGRGHMLSLAGDKKGYRKV
LTYKGEGYGDEVEVVGGEKELLQRFLEIVEEEDPDILLTYNGDGYDFRVLRERAEELGVELTMGRGGS
RLEFARRGRVSSARLGGRVHIDLFSFVNLALAGHLETEVLTLDAVAAELLGERKIEMEMEEMLEKWRR
EEDLGKLARYSLKDSGFTCRLGEQLLPQIYALCNLTAQTPYDCSRMSYGQLVEWFLIKEAHGERIVPNR
PKWKELQKRRELEPYKGGFVREPVVGMHENLAVLDFQSLYPSHASYNIAPETVNCDCCKGGEVEGVR
LCREKRGFIPSLLRGLIEERSRIKEKLEGVEEPLEHRTLDNRQYALKILANSTYGYFGYVGARWYCRDC
ARVTSALGREWIKKVMGMAEEEGFRVIYGDTDSLIIKDGEPRSFLEKVNSQLPGIMNLEMEGRFARGLF
VREKKGRGAKKRYALLDGKGGMKVRGFETVRRDWCSLAKRAQREILYILLSENSVPRATRHARRVIE
RLESKDVSLRDLIIYTSLTKAPGDYETTSPHVSAARKLEEKGRVVKPGSVIMYVVEGKGSISERALPVE
FATIEEVDSEYYIENQIVPAALRVLGVMGVDERELRGGGTQETIEEFF

FIG. 9

SEQ ID NO:3

BR3 polymerase open reading frame sequence

```
atggcaaatcagacaacaaatggtgatcatatggaaggcctgctcctagatagcgattatctcaaa
actcgcaagccccagcaatgagactattcatcaaaaagatgggggaatagtcaccgtcctagat
ccacatttcactcattatttttatgtagaaatctgaaaatcctcaaaaaatagctaaagcgatagag
agggtcgaagcggaaaagtatgggaaaaagtaagcccaaagtcaactaaggttgtcgaacgcaag
tttctcggtgaagagaagaaagtcattaaagtcctagcagacagtccccgagatataactccatta
agaaaagaaatcaaagattttcctgaagtcaagggattttacgagcacgacattcctccagccaga
cgatacctcatagaacacgaattaaccccaatgagcggggtaaaggcagagggagaatcacaaaaa
ggtgattatggcgaggaattagtactcaccaaacgcctgagtcaatcgaaggagcagacgaagaa
ctcaatatcctcgcctttgacatagaaacctacagtcccacaggcaatcctcgcgcgaaaaagat
ccaatagtaatgataagtgtttcagataatcaaggcttagaagaagatccttacatggaaagatttt
gacctaaatctagattatgtggaagttttagatgatgaaaaatcaatgattgagagatttatccaa
ttagttcaagaatgcgatgcagacatcataatgggctacaacacagacctctttgacttcccatac
ctaactcaacgagcagaaaaactagacatcaagctagaactcggtagagacggttcagaaccctca
actaagaaaggcgattgctacagtaaccaaaattgctggcagagtccacgcgggacgtttatgca
atggtcgaattccttcgcgaattggagcaattagattgatagattacacccttgaaaatgtttac
aagcacgtgatagggaaggaaaaacccgatttagaatacagtgacattccaaaagcttgggatgaa
ggagggaaaaagctagagagttagtagagtactcgttatctgacgctaaggcaactctagagcta
ggcactgaaatacttccattattcactgaactgagtcgaaccgtgaaacaatcactctttgatgtt
tcgcgaatgactccaggccaattggtagagtggctcctaatcttcaatgctcataagatcaacgaa
ctcatcctcccgcgcccgctaggacgagaatacaagagacggcgtggtgagacttatattggtggt
tatgtaaaggaaccgacgccaggtcttcatgaggatctcgtagtctttgattttcgctctctatac
ccgaccataatcattactcacaatattgatccagcgacactcgatggggagcgttgtccctcagaa
gaaactgtgacagctccagatcttgaatacgagttctgtcaagatcggaagggtttcattccggag
acattgaaagggcttgttgaaggaagagcaaaattaaagcaggagatgagtcaacttgatgaggag
agtagagaataccaatccctctataatagacaatgggcactcaagatcatagcgaactcattctat
gggatgcttgataccctcgagccagatggtattctaaagaatgtgcagaaagcgttacgagcttc
ggccgtcactatattaaagacacgattgagatggcgaaagacgaaggatttgaagtcatctatggg
gatactgattccctcttcgctaagctcaatgggaaaagtcgagaagatgtcgaaaatttcctgaat
aaggtcaatgagagcttgccagggataatgaaactcgagctggaggattactacaagcgaggagta
ttcgtcaccaaaaaagatacgcaatgatcagcgaggatgacaaaatagtcgttaagggactcgag
ttcgtcaggcgtgactgggcagctctggcgaaaagaactcaagagcaagtcatcgaag
```

BR3 polymerase amino acid sequence

```
MANQTTNGDHMEGLLLDSDYLKTRKPPAMRLFIKKDGGIVTVLDPHPTHYFYVESEKPQKIAKAIE
RVEAEKYGKKVSPKSTKVVERKFLGEEKKVIKVLADSPRDITPLRKEIKDFPEVKGFYEHDIPPAR
RYLIEHELTPMSGVKAEGESQRGDYGEELVLTKPPESIEGADEELNILAFDIETYSPTGNPRAEKD
PIVMISVSDNQELEKILTWKDFDLNLDYVEVLDDEKSMIERFIQLVQECDADIINGYNTDLFDFPY
LTQRAEKLDIKLELGRDGSEPSTKKRRFATVTKIAGRVHADVYAMVEFLSRIGAIRLIDYTLENVY
KHVIGKEKPDLEYSDIPKAWDRGGEKARELVEYSLSDAKATLELGTEILPLFTELSRTVKQSLFDV
SRMTPGQLVEWLLIFKAHKINELILPRPLGREYKRRRGETYIGGYVKEPTPGLSEDLVVFDFRSLY
PTIIITHNIDPATLDGERCPSEETVTAPDLEYEFCQDRKGFIPETLKGLVEGRAKLKQEMSQLDEE
SREYQSLYNRQWALKIIANSFYGMLGYPRAEWYSKECAESVTSPGRHYIKDTIEMAKDEGFEVIYG
DTDSLFAKLNGKSREDVKNFLNKVNESLPGIMKLELEDYYKRGVFVTKKRYAMISEDDKIVVKGLE
FVRRDWAALAKRTQEQVIEAILHDASPEKAAKIVLETTKAIKQGEVDLDDLVIHTQLKKPLDEYKA
RGPHVAAAERLQKLGEEVEPGMTITYIVEKGSGSISDRAIPPSDFEGRDYDPDYYVEKQVLPAVMR
IMEVLDYGEEDLRHEETRQVKLGKFK
```

FIG. 10

```
KOD  ---------------MILDTDYITEDGKPVIRIFKKENGEFKIEYDRTFEPYFYALLKD-DS  46
Pfu  ---------------MILDVDYITEEGKPVIRLFKKENGKFKIEHDRTFRPYIYALLRD-DS  46
Tli  ---------------MILDTDYITKDGKPIIRIFKKENGEFKIELDPHFQPYIYALLKD-DS  46
BR3  MANQTTNGDHMEGLLLDSDYLKTRKPPAMRLFIKKDGGIVTVLDPHFTHYFYVESENPQK    60
                      :;** **;.  *  ;*;* *;;*    *  *  *;  *;
```
N-term

```
KOD  AIEEVKKITAERHGTVVTVKRVEKVQKKFLGRPVEVWKLYFTHPQDVPAIRDKIREHPAV  106
Pfu  KIEEVKKITGERHGKIVRIVDVEKVEKKPLGKPITVWKLYLEHPQDVPTIREKVREHPAV  106
Tli  AIEEIKAIKGERHGKTVRVLDAVKVRKKFLGREVEVWKLIFEHPQDVPAMRGKIREHPAV  106
BR3  IAKAIERVEAERYGKKVSPKSTKVVERKFLGEEKKVIKVLADSPRDITPLRKEIKDFPEV  120
      :  ::  :  .*::*.  *    .  *;:****.    * *;    *;:*;..;:*  **.*
```

```
KOD  IDIYEYDIPFAKRYLIDKGLVPME---------------------------GDEELKML  138
Pfu  VDIFEYDIPFAKRYLIDKGLIPME---------------------------GEEELKIL  138
Tli  VDIYEYDIPFAKRYLIDKGLIPME---------------------------GDEELKLL  138
BR3  KGPYEHDIPPARRYLIEHELTPMSGVKAEGESQKGDYGEELVLTKPPESIEGADEELNIL  180
      . ;;*;***  *;*****;;  *  **.                      .;****;;*
```

```
KOD  AFDISTLYHEGEEFA-EGPILMISYADEE-GARVITWKNVDL---PYVDVVSTEREMIKRF  194
Pfu  AFDISTLYHEGEEFG-KGPIIMISYADEN-EAKVITWKNIDL---PYVEVVSSEREMIKRF  194
Tli  AFDISTFYHEGDEFG-KGEIIMISYADEE-EARVITWKNIDL---PYVDVVSNEREMIKRF  194
BR3  AFDITYSPTGNPRAERDPIVMISVSDNQGLEKILTWKDFDLMLDYVEVLDDEKSMIERF   240
      ******   *;     . ; . *;***  ;*;;    ;;;****;**    **;*;*; **;**
```
Exo

```
KOD  LRVVKEKDPDVLITYNGDNFDFAYLKKRCEKLGINFALGRDG--SEPKIQMMGDSFAVEV  252
Pfu  LRIIREKDPDIIVTYNGDSFDFPYLAKRAEKLGIKLTIGRDG--SEPKMQRIGDMTAVEV  252
Tli  VQVVKEKDPDVIITYNGDNFDLPYLIKRAEKLGVRLVLGRDKEHPEPKIQMMGDSFAVEI  254
BR3  IQLVQECDADIIMGYNTDLFDFPYLTQRAEKLDIKLELGRDG--SEPSTKRRRFATVTKI  298
     ;;::;*  *.*;;; ** * **;;**  ;*.***.;,;    ;***    .**. ;;    ..;;
```

```
KOD  KGRIHFDLYPVIR-----RTINLPTYTLEAVYEAVFGQPKEKVYAEEITTAWETG-ENLE  306
Pfu  KGRIHFDLYHVIT-----RTINLPTYTLEAIFGKPKEKVYAEEIAAIAWETG-ENLE      306
Tli  KGRIHFDLFPVVR-----RTINLPTYTLEAVYEAVLGKTKSKLGAEEIAAIWETE-ESMK  308
BR3  AGRVHADVYAMVEFLSRIGAIRLIDYTLENVYKHVIGKEKPDLEYSDIPKAWDEGGEKAR  358
      **;;* *;; ;;        ;*.*  **** **; ;;*;  * ;;   ;;*.  *;  *, .
```

```
KOD  RVARYSMEDAKVTYELGKEFLPMEAQLSRLIGQSLWDVSRSSTGNLVEWFLLRKAYERNE  366
Pfu  RVAKYSMEDAKATYELGKEFLPMEIQLSRLVGQPLWDVSRSSTGNLVEWFLLRKAYERNE  366
Tli  KLAQYSMEDARATYELGKEFFPMEAELAKLIGQSVWDVSRSSTGNLVEWYLLRVAYARNE  368
BR3  ELVEYSLSDAKATLELGTEILPLFTELSRTVKQSLFDVSMMTPGQLVEWLLIFNAHKINE  418
      .; ..*;**..*.* *;:*  ;:;;   ;  ;*.;;****  ;.;;***** **;  *;  **
```
N-term

```
KOD  LAPNKPDEKELARR--XQSYEGGYVKEPERGLWENIVYLDFRSLYPSIIITHNVSPDTLNR  425
Pfu  VAPNKPSEEEYQRRLRESYTGGFVKEPEKGLWENIVYLDFRALYPSIIITHNVSPDTLNL  426
Tli  LAPNKPDEEEYKRRLRTTYLGGYVKEPEKGLWENIIYLDFRSLYPSIIVTHNVSPDTLEK  428
BR3  LILPRPLGREYKRRRGETYIGGYVKEPTPGLHEDLVVFDFRSLYPTIIITHNIDPATLDG  478
      ;    ;*  .*  **  ;*  **;****  ** *;;;  ;****;****;**;;***;.* **;
```
Palm

```
KOD  EGCKEYD--VAPQVGHRFCKDFPGFIPSLLGDLLEERQKIKKMKAT-IDPIEKLLDYR    482
Pfu  EGCKNYD--IAPQVGHRFCKDIPGFIPSLLGBLLEERQKIKTMKMET-QDPIEKILLDYR  483
Tli  EGCKNYD--VAPIVGYRFCKDFPGFIPSILGDLIAMSQDIKKKMSST-IDPIESXMLDYR  485
BR3  ERCPSEETVTAPDLEYEFCQDRKGFIPETLKGLVEGRAKLSQEMSQLDEESREYQSLYNR  538
      *  *    .    **  ;.**;* ****  **  *;       *  .;*  ;*  .    *    *  *
```
Finger

```
KOD  QRAIKILANSYYGYYGYARARWYCKECAESVTAWGREYITMTIKEIEEKYGFKVIYSDTD  542
Pfu  QRAIKLLANSFYGYYGYAKARWYCKECAESVTAWGRKYIELVWKELEEKFGFKVLYIDTD  543
Tli  QRAIKLLANSYYGYYGMGYPRARWYSKECAESVTAWGRHYIEMTIREIEEKFGFKVLYADTD  545
BR3  QWALKIIANSFYGMLGYPRARWYSKECAESVTSFGRHYIKDTIEMAKDE-GFEVIYGDTD  597
      * *;;*;:***;:**  **.;*****.********;:**.**     . . . ;;; **;*;* ***
```
Palm

```
KOD  GFFATIPGADAETVKKKAMEFLKYINAKLPGALELEYEGFYKRGFFVTKKKYAVIDEEGK  602
Pfu  GLYATIPGGESEEIKKKALEFVKYINSKLPGLLELEYEGFYKRGFFVTKKRYAVIDEEGK  603
Tli  GFYATIPGEKPELIKKKAREFLNYINKLPGLLELEYEGFYLRGFFVTKKRYAVIDEEGK  605
BR3  SLFAKLNGKSREDVEN----FLNKVNESLPGIMKLELEDYYKRGVFVTKKRYAMISEDDK  653
      .;;*.;  *  . *  ;;;   *;;  ;*  .***  ;;**  *.;**  **.*****;*:*.*;;;
```

```
KOD  ITTRGLEIVRRDWSEIAKETQARVLEALLKDGDVEKAVRIVKEVTEKLSKYEVPPEKLVI  662
Pfu  VITRGLEIVRRDWSEIAKETQARVLETILKHGDVEEAVRIVKEVIQKLANYEIPPEKLAI  663
Tli  ITTRGLEVVRRDWSEIAKETQAKVLEAILKEGSVEKAVEVVRDVVEKIARYRVPLEKLVI  665
BR3  IVVKGLEFVRRDWAALAKRTQEQVIEAILHDASPEKAAKIVLETTKAIKQGEVDLDDLVI  713
      :  .;:***.******:* ;:**;**  ;*;*;;*;;*.  ..  *;..*;;  ;;  ;;  ;.*;*
```

```
KOD  HEQITRDLKDYKATGPHVAVAKRLAARGVKIRPGTVISYIVLKGSGRIGDRAIPFDEFDP  722
Pfu  YEQITRPLHEYKAIGPHVAVAKKLAAKGVKIKPGMVIGYIVLRGDGPISNRAILAEEYDP  723
Tli  HEQITRDLKDYKAIGPHVAIAKRLAARGIKVKPGTIISYIVLKGSGKISDRVILLTEYDP  725
BR3  HTQLKKPLDEYKARGPHVAAAERLQKLGEEVEPGMTITYIVEKGSGSISDRAIPFPSDFG  773
      ; *;;.; *;:**** *****  ****  **;;*  *;;;** ;***  ;*;*;*.*   ;;;
```

```
KOD  TKHKYDAEYYIENQVLPAVERILRAFGYRKEDLRYQKTRQVGLSAWLKPKGT 774
Pfu  KKHKYDAEYYIENQVLPAVLRILEGFGYRKEDLRYQKTRQVGLTSWLNIKKS 775
Tli  RKHKYDPYYIENQVLPAVLRILEAFGYRKEDLRYQSSKQTGLDAWLKR---  774
BR3  R---DYDPYYVENQVLPAVMRIMEVLDYGEEDLRHEETRQVKLGKFK----  818
      .**;**;********  **;;  ;.;*    ;  *****;;.;;*.  *    ;
```
Thumb

SEQUENCE LISTING

<160> NUMBER OF SEQ ID NOS: 17

<210> SEQ ID NO 1
<211> LENGTH: 699
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 1

Met Arg Glu Thr Ser Glu Gly Trp Leu Leu Asp Ala Tyr Ile Glu Gly
1               5                   10                  15

Arg Tyr Ala Val Leu Trp Leu Lys Ser Ile Asp Gly Thr Val His Arg
            20                  25                  30

Leu Arg Glu Arg Tyr Arg Pro Cys Phe Tyr Ala Glu Pro Arg Asp Asp
        35                  40                  45

Cys Arg Ile Glu Asp Ala Ala Ser Thr Ile Glu Thr His Pro Ala Val
    50                  55                  60

His Ser Ala Leu Glu Val Glu Arg Tyr Ala Thr Leu Arg Arg Arg Glu
65                  70                  75                  80

Val Lys Arg Val Val Lys Val Ser Val Glu Ser Thr Asp Glu Leu Asp
                85                  90                  95

Gln Ala Val Ala Phe Ala Arg Arg His Gln Met Val Arg Glu Leu Tyr
            100                 105                 110

Asn Val Gly Leu Thr Pro Val Gln Trp Tyr Leu Phe Gln Leu Asp Ala
        115                 120                 125

Ala Pro Ser Ser His Val Glu Trp Thr Arg Arg Gly Gly Val Leu Glu
    130                 135                 140

Ser Ile Thr Val Leu Asp Gly Gly Leu Arg Val Glu Pro Pro Phe
145                 150                 155                 160

Lys Pro Ile Ile Ile Gln Thr Ser Lys Pro Pro Ile Glu Glu Val Asp
                165                 170                 175

Leu Tyr Asp Asp Cys Gly Ser His Leu Ala Ala Leu Arg Gly Cys Glu
            180                 185                 190

Arg Glu Val Leu Ser Glu Leu Gln Gly Ala Val Thr Glu Ile Asp Pro
        195                 200                 205

Asp Ile Val Ala Met Val Asp Gly Val Asp Thr Ile Arg Arg Leu Arg
    210                 215                 220

Gln Arg Ala Gly Ala Lys Gly Val Asp Leu Cys Val Gly Arg Leu Gly

-continued

```
               225                 230                 235                 240
Asp Ala Ser His Gly Arg Val Ala Leu Glu Asn Arg Trp Phe Arg Asp
                    245                 250                 255

Leu Gly Val Val Gly Leu Val Glu Arg Ala Arg Phe Ala Met Ala Pro
                    260                 265                 270

Met Gly Val Cys Ala Gly Trp Ala Gly Arg Thr Val Asp Ser Arg
                275                 280                 285

Gln Cys Tyr Glu Ala Asp Arg Leu Gly Val Leu Val Ser Glu Met Lys
        290                 295                 300

Gly Gly Tyr Ala Tyr Ala Ala Thr Ala Trp Glu Leu Leu Phe Arg Asp
305                 310                 315                 320

Arg Gly Gly Met Val Leu Ser Pro Glu Met Gly Leu His Glu Asn Val
                    325                 330                 335

Gly Val Leu Asp Phe Glu Ser Met Tyr Pro Asn Ile Ile Val Thr Arg
                    340                 345                 350

Asn Val Ser Tyr Glu Asn Ile Thr Pro Asn Gly Val Glu Arg Gly Pro
                355                 360                 365

Gln Gly Phe Leu Gly Gly Phe Thr Arg Arg Phe Leu Arg Arg Arg Leu
        370                 375                 380

His Tyr Lys His Leu Arg Ser Ser Tyr Pro Thr Asp Ser Arg Glu Trp
385                 390                 395                 400

Arg Trp Cys Glu Gln Arg Gln Arg Ser Leu Lys Leu Met Leu Val Val
                    405                 410                 415

Ile Tyr Gly Tyr Ser Gly Cys Tyr Ala Asn Arg Phe Gly Asn Val Arg
                    420                 425                 430

Val Phe Gln Glu Ile Asn Arg Val Ala Arg Gln Ala Leu Val Glu Ser
                435                 440                 445

Leu Asn Thr Ala Leu Ser Arg Gly Tyr Arg Val Val Tyr Gly Asp Ser
        450                 455                 460

Asp Ser Leu Phe Thr Ala Lys Gln Gly Ala Thr Arg Glu Asp Tyr Leu
465                 470                 475                 480

Gly Leu Ala Glu Glu Ile Ala Glu Ala Thr Gly Leu Pro Ile Thr Leu
                    485                 490                 495

Asp Arg His Phe Lys Tyr Leu Val Leu Leu Pro Gln Ala Gly Asp Pro
                    500                 505                 510

Glu Met Gly Ala Ala Arg Arg Tyr Tyr Gly Lys Leu Thr Asp Gly Thr
                515                 520                 525

Leu Phe Tyr Arg Gly Ile Glu Leu Arg Arg Arg Asp Thr Pro Pro Tyr
        530                 535                 540

Ile Arg Arg Leu Gln Arg Arg Val Met Glu Thr Leu Phe Asn Ala Asp
545                 550                 555                 560

Thr Ala Glu Glu Val Arg Gly Arg Gln Leu Pro Lys Ala Leu Glu Leu
                    565                 570                 575

Val Lys Ala Ala Cys Ala Glu Leu Leu Arg Gly Gln Val Asp Pro Arg
                    580                 585                 590

Glu Leu Val Val Ser Lys Arg Leu Arg Arg Pro Gly Asp Tyr Ala
                595                 600                 605

Ser Lys Gln Pro His Val Ala Ala Gln Leu Glu Gly Leu Glu Glu
        610                 615                 620

Gly Tyr Ser Glu Phe Leu Tyr Val Asn Ser Glu Arg Arg Asn Pro Tyr
625                 630                 635                 640

Ile Arg Val Met Pro Ala Ser Met Val Asn Gly Gly His His Thr Ile
                    645                 650                 655
```

```
Asp Arg Ala Trp Tyr Ser Ser Met Ala Arg Arg Ala Ala Glu Asn Ile
            660                 665                 670

Leu Arg Pro Phe Leu Asp Glu Gly Ser Asn Gly Gly Lys Leu Arg
        675                 680                 685

Val Ser Arg Leu Asp Thr Phe Phe Ser Arg Arg
    690                 695

<210> SEQ ID NO 2
<211> LENGTH: 783
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Met Lys Ala Tyr Leu Leu Asp Ile Asp Tyr Thr Thr Val Lys Asp Arg
1               5                   10                  15

Ala Glu Val Lys Leu Tyr Leu Arg Gly Glu Gly Arg Leu Glu Val
            20                  25                  30

Tyr Asp Arg Asn Phe Leu Pro Tyr Phe Tyr Val Leu Gly Asp Glu Val
            35                  40                  45

Glu Glu Lys Leu Leu Glu Glu Gly Ala Leu Lys Val Glu Gly Arg Arg
    50                  55                  60

Lys Lys Leu Leu Gly Arg Glu Val Lys Ala Leu Gln Val Phe Ala Ser
65                  70                  75                  80

His Pro Gln Glu Val Pro Glu Leu Arg Asn Lys Val Lys Lys Ile Glu
                85                  90                  95

Gly Val Asp Leu Thr Leu Glu Asp Asp Ile Leu Phe Thr Arg Arg Tyr
            100                 105                 110

Leu Ile Asp Arg Gly Met Lys Pro Leu Thr Trp Tyr Asp Phe Asp Val
        115                 120                 125

Arg Glu Glu Gly Gly Lys Tyr Tyr Leu Gln Gly Phe Lys Glu Ile Glu
    130                 135                 140

Gly Gly Ser Pro Gly Leu Arg Thr Val Ala Leu Asp Ile Glu Val Tyr
145                 150                 155                 160

Asn Pro Gly Gly Val Pro Arg Pro Glu Glu Asp Pro Ile Ile Met Val
                165                 170                 175

Ser Leu Ala Gly Ser Gly Gly Leu Lys Lys Val Leu Thr Trp Lys Asp
            180                 185                 190

Glu Gly Glu Val Pro Gly Phe Val Glu Val Leu Ser Ser Glu Gly Ala
        195                 200                 205

Met Leu Gly Arg Leu Glu Glu Ile Phe Lys Glu Glu Ile Asp Val
    210                 215                 220

Val Val Gly Tyr Asn Thr Asp Asn Phe Asp Phe Pro Tyr Ile Lys Lys
225                 230                 235                 240

Arg Leu Gln Thr Leu Asp Met Glu Leu Gln Leu Gly Gly Asp Asn Ile
                245                 250                 255

Lys Ile Lys Gly Arg Lys Ser Leu Pro Gln Ala Ala Leu Gly Gly Leu
            260                 265                 270

Pro His Leu Asp Leu Tyr Pro Ile Val Arg Arg Asn Val Arg Leu Asn
        275                 280                 285

Ser Tyr Val Leu Glu Asn Val Leu Lys Glu Val Leu Lys Glu Glu Lys
    290                 295                 300
```

```
Glu Lys Ile Pro Asn Glu Lys Ile Trp Glu Tyr Trp Asp Ala Gly Gly
305                 310                 315                 320
Glu Lys Leu Glu Lys Leu Phe His Tyr Ser Leu Glu Asp Ala Glu Gly
                325                 330                 335
Thr Leu Arg Leu Ser Gln Arg Phe Val Pro Leu Tyr Val Gln Leu Ser
            340                 345                 350
Ala Ile Val Gly Gln Cys Leu Tyr Asp Thr Ser Arg Met Thr Thr Gly
        355                 360                 365
Gln Met Val Glu Trp Tyr Leu Met Arg Ile Ala Ser Arg Ala Ser Glu
    370                 375                 380
Leu Ile Pro Asn Arg Pro Lys Gly Glu Leu Lys Gly Arg Phe Ser
385                 390                 395                 400
Thr Thr Tyr Ala Gly Gly Tyr Val His Gln Pro Arg Lys Gly Met Val
                405                 410                 415
Arg Asp Ile Ala Val Phe Asp Phe Arg Ser Leu Tyr Pro Ser Ile Ile
            420                 425                 430
Val Thr His Asn Ile Asp Pro Ser Thr Leu Arg Glu Gly Val Gly Cys
        435                 440                 445
Glu Glu Asn Lys Ala Pro Ser Leu Asp Tyr Cys Phe Ser Arg Glu Glu
    450                 455                 460
Lys Gly Phe Ile Pro Ser Ile Leu Glu Gly Leu Val Asn Trp Arg Gly
465                 470                 475                 480
Glu Val Lys Lys Lys Met Glu Gly Lys Gly Glu Glu Leu Arg Thr
                485                 490                 495
Leu Asp Phe Thr Gln Lys Ala Leu Lys Ile Leu Ser Asn Ser Phe Tyr
            500                 505                 510
Gly Tyr Met Gly Tyr Pro Arg Ala Arg Trp Tyr Arg Glu Cys Ala
        515                 520                 525
Glu Ser Val Ala Ser Phe Ala Arg Glu Tyr Ile Lys Lys Val Met Ala
    530                 535                 540
Thr Ala Lys Glu Glu Phe Gly Leu Glu Val Val Tyr Gly Asp Thr Asp
545                 550                 555                 560
Ser Leu Phe Val Leu Leu Pro Gly Lys Glu Lys Ala Arg Ala Glu Glu
                565                 570                 575
Phe Leu Glu His Val Asn Arg Ser Met Pro Gly Ile Ile Gln Leu Glu
            580                 585                 590
Leu Glu Gly Phe Tyr Leu Arg Gly Leu Phe Val Ser Lys Lys Arg Tyr
        595                 600                 605
Ala Leu Leu Asp Glu Lys Gly Lys Ile Thr Val Lys Gly Leu Glu Phe
    610                 615                 620
Val Arg Arg Asp Trp Ala Pro Ile Ala Arg Glu Thr Gln Gln Lys Val
625                 630                 635                 640
Leu Glu Ile Leu Leu Lys Glu Gly Asp Glu Gly Lys Ala Leu Arg Leu
                645                 650                 655
Val Arg Glu Val Ile Glu Asn Ile Lys Arg Arg Glu Val Thr Leu Asn
            660                 665                 670
Gln Ile Ser Ile Tyr Thr Gln Leu Thr Arg Lys Val Glu Ser Tyr Glu
        675                 680                 685
Gly Lys Glu Pro His Val Gly Ala Ala Lys Lys Leu Gln Asp Glu Gly
    690                 695                 700
Tyr Lys Val Lys Ala Gly Ser Ile Ile Gly Tyr Ile Val Ala Lys Gly
705                 710                 715                 720
Arg Lys Gly Glu Lys Ile Ser Glu Arg Thr Leu Pro Val Glu Leu Ala
```

```
                        725                 730                 735
Ser Val Glu Asp Tyr Asp Pro Asn Tyr Tyr Ile Glu Asn Gln Ile Leu
            740                 745                 750

Pro Ala Val Gly Arg Ile Phe Asp Ala Leu Gly Tyr Arg Arg Asp Tyr
            755                 760                 765

Ile Lys Thr Gly Val Glu Gln Arg Ser Leu Gly Lys Trp Ile Ser
770                 775                 780

<210> SEQ ID NO 3
<211> LENGTH: 818
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Met Ala Asn Gln Thr Thr Asn Gly Asp His Met Glu Gly Leu Leu Leu
1               5                   10                  15

Asp Ser Asp Tyr Leu Lys Thr Arg Lys Pro Ala Met Arg Leu Phe
            20                  25                  30

Ile Lys Lys Asp Gly Gly Ile Val Thr Val Leu Asp Pro His Phe Thr
            35                  40                  45

His Tyr Phe Tyr Val Glu Ser Glu Asn Pro Gln Lys Ile Ala Lys Ala
        50                  55                  60

Ile Glu Arg Val Glu Ala Glu Lys Tyr Gly Lys Val Ser Pro Lys
65                  70                  75                  80

Ser Thr Lys Val Val Glu Arg Lys Phe Leu Gly Glu Lys Lys Val
                85                  90                  95

Ile Lys Val Leu Ala Asp Ser Pro Arg Asp Ile Thr Pro Leu Arg Lys
            100                 105                 110

Glu Ile Lys Asp Phe Pro Glu Val Lys Gly Phe Tyr Glu His Asp Ile
            115                 120                 125

Pro Pro Ala Arg Arg Tyr Leu Ile Glu His Glu Leu Thr Pro Met Ser
        130                 135                 140

Gly Val Lys Ala Glu Gly Glu Ser Gln Lys Gly Asp Tyr Gly Glu Glu
145                 150                 155                 160

Leu Val Leu Thr Lys Pro Pro Glu Ser Ile Glu Gly Ala Asp Glu Glu
                165                 170                 175

Leu Asn Ile Leu Ala Phe Asp Ile Glu Thr Tyr Ser Pro Thr Gly Asn
            180                 185                 190

Pro Arg Ala Glu Lys Asp Pro Ile Val Met Ile Ser Val Ser Asp Asn
        195                 200                 205

Gln Gly Leu Glu Lys Ile Leu Thr Trp Lys Asp Phe Asp Leu Asn Leu
    210                 215                 220

Asp Tyr Val Glu Val Leu Asp Glu Lys Ser Met Ile Glu Arg Phe
225                 230                 235                 240

Ile Gln Leu Val Gln Glu Cys Asp Ala Asp Ile Ile Met Gly Tyr Asn
                245                 250                 255

Thr Asp Leu Phe Asp Phe Pro Tyr Leu Thr Gln Arg Ala Glu Lys Leu
            260                 265                 270

Asp Ile Lys Leu Glu Leu Gly Arg Asp Gly Ser Glu Pro Ser Thr Lys
        275                 280                 285

Lys Arg Arg Phe Ala Thr Val Thr Lys Ile Ala Gly Arg Val His Ala
    290                 295                 300
```

```
Asp Val Tyr Ala Met Val Glu Phe Leu Ser Arg Ile Gly Ala Ile Arg
305                 310                 315                 320

Leu Ile Asp Tyr Thr Leu Glu Asn Val Tyr Lys His Val Ile Gly Lys
                325                 330                 335

Glu Lys Pro Asp Leu Glu Tyr Ser Asp Ile Pro Lys Ala Trp Asp Glu
            340                 345                 350

Gly Gly Glu Lys Ala Arg Glu Leu Val Glu Tyr Ser Leu Ser Asp Ala
                355                 360                 365

Lys Ala Thr Leu Glu Leu Gly Thr Glu Ile Leu Pro Leu Phe Thr Glu
370                 375                 380

Leu Ser Arg Thr Val Lys Gln Ser Leu Phe Asp Val Ser Arg Met Thr
385                 390                 395                 400

Pro Gly Gln Leu Val Glu Trp Leu Leu Ile Phe Asn Ala His Lys Ile
                405                 410                 415

Asn Glu Leu Ile Leu Pro Arg Pro Leu Gly Arg Glu Tyr Lys Arg Arg
                420                 425                 430

Arg Gly Glu Thr Tyr Ile Gly Tyr Val Lys Glu Pro Thr Pro Gly
                435                 440                 445

Leu His Glu Asp Leu Val Val Phe Asp Phe Arg Ser Leu Tyr Pro Thr
450                 455                 460

Ile Ile Ile Thr His Asn Ile Asp Pro Ala Thr Leu Asp Gly Glu Arg
465                 470                 475                 480

Cys Pro Ser Glu Glu Thr Val Thr Ala Pro Asp Leu Glu Tyr Glu Phe
                485                 490                 495

Cys Gln Asp Arg Lys Gly Phe Ile Pro Glu Thr Leu Lys Gly Leu Val
                500                 505                 510

Glu Gly Arg Ala Lys Leu Lys Gln Glu Met Ser Gln Leu Asp Glu Glu
                515                 520                 525

Ser Arg Glu Tyr Gln Ser Leu Tyr Asn Arg Gln Trp Ala Leu Lys Ile
530                 535                 540

Ile Ala Asn Ser Phe Tyr Gly Met Leu Gly Tyr Pro Arg Ala Arg Trp
545                 550                 555                 560

Tyr Ser Lys Glu Cys Ala Glu Ser Val Thr Ser Phe Gly Arg His Tyr
                565                 570                 575

Ile Lys Asp Thr Ile Glu Met Ala Lys Asp Glu Gly Phe Glu Val Ile
                580                 585                 590

Tyr Gly Asp Thr Asp Ser Leu Phe Ala Lys Leu Asn Gly Lys Ser Arg
                595                 600                 605

Glu Asp Val Glu Asn Phe Leu Asn Lys Val Asn Glu Ser Leu Pro Gly
                610                 615                 620

Ile Met Lys Leu Glu Leu Glu Asp Tyr Tyr Lys Arg Gly Val Phe Val
625                 630                 635                 640

Thr Lys Lys Arg Tyr Ala Met Ile Ser Glu Asp Asp Lys Ile Val Val
                645                 650                 655

Lys Gly Leu Glu Phe Val Arg Arg Asp Trp Ala Ala Leu Ala Lys Arg
                660                 665                 670

Thr Gln Glu Gln Val Ile Glu Ala Ile Leu His Asp Ala Ser Pro Glu
                675                 680                 685

Lys Ala Ala Lys Ile Val Leu Glu Thr Thr Lys Ala Ile Lys Gln Gly
                690                 695                 700

Glu Val Asp Leu Asp Asp Leu Val Ile His Thr Gln Leu Lys Lys Pro
705                 710                 715                 720
```

-continued

```
Leu Asp Glu Tyr Lys Ala Arg Gly Pro His Val Ala Ala Glu Arg
            725                 730                 735

Leu Gln Lys Leu Gly Glu Glu Val Glu Pro Gly Met Thr Ile Thr Tyr
        740                 745                 750

Ile Val Glu Lys Gly Ser Gly Ser Ile Ser Asp Arg Ala Ile Pro Pro
            755                 760                 765

Ser Asp Phe Glu Gly Arg Asp Tyr Asp Pro Asp Tyr Tyr Val Glu Asn
    770                 775                 780

Gln Val Leu Pro Ala Val Met Arg Ile Met Glu Val Leu Asp Tyr Gly
785                 790                 795                 800

Glu Glu Asp Leu Arg His Glu Glu Thr Arg Gln Val Lys Leu Gly Lys
                805                 810                 815

Phe Lys

<210> SEQ ID NO 4
<211> LENGTH: 799
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Met Glu Glu Lys Ile Tyr Leu Leu Asp Leu Asp Tyr Ile Glu Glu Glu
1               5                   10                  15

Thr Glu Arg Gly Met Glu Ala Thr Val Arg Leu Trp Gly Lys Asn Gly
            20                  25                  30

Glu Gly Lys Ser Val Val Ala Trp Asp Arg Ala Phe Asp Pro Tyr Phe
        35                  40                  45

Tyr Tyr Val Pro Gly Asp Phe Pro Leu Ala Lys Glu Arg Leu Glu Gly
    50                  55                  60

Val Asp Glu Pro Arg Ile Lys Gly Val Glu Ala Glu Lys Ile Leu
65                  70                  75                  80

Gly Lys Glu Glu Val Lys Ala Leu Arg Val Tyr Gly Ser Arg Pro Ser
                85                  90                  95

Asp Leu Pro Lys Leu Arg Asp Lys Leu Lys Gly Glu Gly Phe Asp Gly
            100                 105                 110

Glu Arg Phe Tyr Glu Tyr Gly Met Ser Phe Tyr Arg Gln Tyr Val Val
        115                 120                 125

Ser Lys Gly Leu Leu Pro Ala Ser Trp Val Leu Val Lys Gly Lys Glu
    130                 135                 140

Val Glu Lys Glu Gly Phe Asp Leu Ala Phe Glu Ala Gly Glu Val Gln
145                 150                 155                 160

Ala Leu Glu Gly Glu Glu Ala Pro Leu Lys Thr Leu Ala Phe Asp
                165                 170                 175

Leu Glu Thr Tyr Glu Ser Gln Glu Gly Arg Gly Ile Ile Met Leu Ser
            180                 185                 190

Leu Ala Gly Asp Lys Lys Gly Tyr Arg Lys Val Leu Thr Tyr Lys Gly
        195                 200                 205

Glu Gly Tyr Gly Asp Glu Val Glu Val Val Gly Glu Lys Glu Leu
    210                 215                 220

Leu Gln Arg Phe Leu Glu Ile Val Glu Glu Asp Pro Asp Ile Leu
225                 230                 235                 240

Leu Thr Tyr Asn Gly Asp Gly Tyr Asp Phe Arg Val Leu Arg Glu Arg
                245                 250                 255
```

-continued

```
Ala Glu Glu Leu Gly Val Glu Leu Thr Met Gly Arg Gly Gly Ser Arg
            260                 265                 270

Leu Glu Phe Ala Arg Arg Gly Arg Val Ser Ser Ala Arg Leu Gly Gly
        275                 280                 285

Arg Val His Ile Asp Leu Phe Ser Phe Val Asn Leu Ala Leu Ala Gly
    290                 295                 300

His Leu Glu Thr Glu Val Leu Thr Leu Asp Ala Val Ala Ala Glu Leu
305                 310                 315                 320

Leu Gly Glu Arg Lys Ile Glu Met Glu Met Glu Met Leu Glu Lys
                325                 330                 335

Trp Arg Arg Glu Glu Asp Leu Gly Lys Leu Ala Arg Tyr Ser Leu Lys
            340                 345                 350

Asp Ser Gly Ile Thr Cys Arg Leu Gly Glu Gln Leu Leu Pro Gln Ile
        355                 360                 365

Tyr Ala Leu Cys Asn Leu Thr Ala Gln Thr Pro Tyr Asp Cys Ser Arg
    370                 375                 380

Met Ser Tyr Gly Gln Leu Val Glu Trp Phe Leu Ile Lys Glu Ala His
385                 390                 395                 400

Gly Glu Arg Ile Val Pro Asn Arg Pro Lys Trp Lys Glu Leu Gln Lys
                405                 410                 415

Arg Arg Glu Leu Glu Pro Tyr Lys Gly Gly Phe Val Arg Glu Pro Val
            420                 425                 430

Val Gly Met His Glu Asn Leu Ala Val Leu Asp Phe Gln Ser Leu Tyr
        435                 440                 445

Pro Ser Ile Ile Ala Ser Tyr Asn Ile Ala Pro Glu Thr Val Asn Cys
    450                 455                 460

Asp Cys Cys Lys Gly Gly Glu Val Gly Val Arg Leu Cys Arg Glu
465                 470                 475                 480

Lys Arg Gly Phe Ile Pro Ser Leu Leu Arg Gly Leu Ile Glu Glu Arg
                485                 490                 495

Ser Arg Ile Lys Glu Lys Leu Glu Gly Val Glu Pro Leu Glu His
            500                 505                 510

Arg Thr Leu Asp Asn Arg Gln Tyr Ala Leu Lys Ile Leu Ala Asn Ser
        515                 520                 525

Thr Tyr Gly Tyr Phe Gly Tyr Val Gly Ala Arg Trp Tyr Cys Arg Asp
    530                 535                 540

Cys Ala Arg Val Thr Ser Ala Leu Gly Arg Glu Trp Ile Lys Lys Val
545                 550                 555                 560

Met Gly Met Ala Glu Glu Gly Phe Arg Val Ile Tyr Gly Asp Thr
                565                 570                 575

Asp Ser Leu Ile Ile Lys Asp Gly Glu Pro Arg Ser Phe Leu Glu Lys
            580                 585                 590

Val Asn Ser Gln Leu Pro Gly Ile Met Asn Leu Glu Met Glu Gly Arg
        595                 600                 605

Phe Ala Arg Gly Leu Phe Val Arg Glu Lys Lys Gly Arg Gly Ala Lys
    610                 615                 620

Lys Arg Tyr Ala Leu Leu Asp Gly Lys Gly Gly Met Lys Val Arg Gly
625                 630                 635                 640

Phe Glu Thr Val Arg Arg Asp Trp Cys Ser Leu Ala Lys Arg Ala Gln
                645                 650                 655

Arg Glu Ile Leu Tyr Ile Leu Leu Ser Glu Asn Ser Val Pro Arg Ala
            660                 665                 670
```

Thr Arg His Ala Arg Arg Val Ile Glu Arg Leu Glu Ser Lys Asp Val
            675                 680                 685

Ser Leu Arg Asp Leu Ile Ile Tyr Thr Ser Leu Thr Lys Ala Pro Gly
        690                 695                 700

Asp Tyr Glu Thr Thr Ser Pro His Val Ser Ala Ala Arg Lys Leu Glu
705                 710                 715                 720

Glu Lys Gly Arg Val Val Lys Pro Gly Ser Val Ile Met Tyr Val Val
                725                 730                 735

Val Glu Gly Lys Gly Ser Ile Ser Glu Arg Ala Leu Pro Val Glu Phe
            740                 745                 750

Ala Thr Ile Glu Glu Val Asp Ser Glu Tyr Tyr Ile Glu Asn Gln Ile
        755                 760                 765

Val Pro Ala Ala Leu Arg Val Leu Gly Val Met Gly Val Asp Glu Arg
    770                 775                 780

Glu Leu Arg Gly Gly Gly Thr Gln Glu Thr Ile Glu Glu Phe Phe
785                 790                 795

<210> SEQ ID NO 5
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 5
caccatggca aatcagacaa caaatgg                                    27

<210> SEQ ID NO 6
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 6
ttatttgaat tttccgagtt ttacttgtcg                                 30

<210> SEQ ID NO 7
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
gccaagcgca cggacgacga gaattcggga ccgga                           35

<210> SEQ ID NO 8
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 8
tccggtcccg aattc                                                 15

<210> SEQ ID NO 9
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
tccggtcccg aattg                                                    15

<210> SEQ ID NO 10
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 10
tccggtcccg aatcg                                                    15

<210> SEQ ID NO 11
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11
tccggtcccg aagcg                                                    15

<210> SEQ ID NO 12
<211> LENGTH: 47
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Phe Asp Asn Gly Glu Tyr Ala His Glu Ile Leu Asn Gly Asp Ile His
1               5                   10                  15

Thr Lys Asn Gln Ile Ala Ala Glu Leu Pro Thr Arg Asp Asn Ala Lys
            20                  25                  30

Thr Phe Ile Tyr Gly Phe Leu Tyr Gly Ala Gly Asp Glu Lys Ile
        35                  40                  45

<210> SEQ ID NO 13
<211> LENGTH: 60
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Ala Leu Lys Ile Ile Ala Asn Ser Phe Tyr Gly Met Leu Gly Tyr Pro
1               5                   10                  15

Arg Ala Arg Trp Tyr Ser Lys Glu Cys Ala Glu Ser Val Thr Ser Phe
            20                  25                  30

Gly Arg His Tyr Ile Lys Asp Thr Ile Glu Met Ala Lys Asp Glu Gly
        35                  40                  45

Phe Glu Val Ile Tyr Gly Asp Thr Asp Ser Leu Phe
    50                  55                  60

<210> SEQ ID NO 14
<211> LENGTH: 2038
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 14

```
atggcaaatc agacaacaaa tggtgatcat atggaaggcc tgctcctaga tagcgattat      60
ctcaaaactc gcaagccccc agcaatgaga ctattcatca aaaagatgg gggaatagtc     120
accgtcctag atccacattt cactcattat ttttatgtag aatctgaaaa tcctcaaaaa     180
atagctaaag cgatagagag ggtcgaagcg gaaaagtatg gaaaaaagt aagcccaaag     240
tcaactaagg ttgtcgaacg caagtttctc ggtgaagaga agaaagtcat taaagtccta     300
gcagacagtc cccgagatat aactccatta gaaaagaaa tcaaagattt tcctgaagtc     360
aagggatttt acgagcacga cattcctcca gccagacgat acctcataga acacgaatta     420
accccaatga gcggggtaaa ggcagaggga gaatcacaaa aaggtgatta tggcgaggaa     480
ttagtactca ccaaaccgcc tgagtcaatc gaaggagcag acgaagaact caatatcctc     540
gcctttgaca tagaaaccta cagtcccaca ggcaatcctc gcgccgaaaa agatccaata     600
gtaatgataa gtgtttcaga taatcaaggc ttagagaaga tccttacatg gaaagatttt     660
gacctaaatc tagattatgt ggaagtttta gatgatgaaa atcaatgat tgagagattt     720
atccaattag ttcaagaatg cgatgcagac atcataatgg gctacaacac agacctcttt     780
gacttcccat acctaactca acgagcagaa aaactagaca tcaagctaga actcggtaga     840
gacggttcag aaccctcaac taagaaaagg cgattcgcta cagtaaccaa aattgctggc     900
agagtccacg cggacgttta tgcaatggtc gaattccttt cgcgaattgg agcaattaga     960
ttgatagatt acacccttga aatgtttac aagcacgtga tagggaagga aaaacccgat    1020
ttagaataca gtgacattcc aaaagcttgg gatgaaggag gggaaaaagc tagagagtta    1080
gtagagtact cgttatctga cgctaaggca actctagagc taggcactga aatacttcca    1140
ttattcactg aactgagtcg aaccgtgaaa caatcactct tgatgtttc gcgaatgact    1200
ccaggccaat tggtagagtg gctcctaatc ttcaatgctc ataagatcaa cgaactcatc    1260
ctcccgcgcc cgctaggacg agaatacaag agacggcgtg gtgagactta tattggtggt    1320
tatgtaaagg aaccgacgcc aggtcttcat gaggatctcg tagtctttga ttttcgctct    1380
ctataccga ccataatcat tactcacaat attgatccag cgacactcga tggggagcgt    1440
tgtccctcag aagaaactgt gacagctcca gatcttgaat acgagttctg tcaagatcgg    1500
aagggtttca ttccggagac attgaaaggg cttgttgaag aagagcaaa attaaagcag    1560
gagatgagtc aacttgatga ggagagtaga gaataccaat ccctctataa tagacaatgg    1620
gcactcaaga tcatagcgaa ctcattctat gggatgcttg ataccctcg agccagatgg    1680
tattctaaag aatgtgcaga aagcgttacg agcttcggcc gtcactatat taagacacg    1740
```

-continued

```
attgagatgg cgaaagacga aggatttgaa gtcatctatg gggatactga ttccctcttc    1800
gctaagctca atgggaaaag tcgagaagat gtcgaaaatt tcctgaataa ggtcaatgag    1860
agcttgccag ggataatgaa actcgagctg gaggattact acaagcgagg agtattcgtc    1920
accaaaaaaa gatacgcaat gatcagcgag gatgacaaaa tagtcgttaa gggactcgag    1980
ttcgtcaggc gtgactgggc agctctggcg aaaagaactc aagagcaagt catcgaag     2038
```

<210> SEQ ID NO 15
<211> LENGTH: 774
<212> TYPE: PRT
<213> ORGANISM: Thermococcus kodakaraensis

<400> SEQUENCE: 15

```
Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Glu Val Lys Lys Ile Thr Ala Glu Arg His Gly Thr Val Val Thr
    50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Ile Asp Ile Tyr Glu Tyr
            100                 105                 110

Asp Ile Pro Phe Ala Lys Arg Tyr Leu Ile Asp Lys Gly Leu Val Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
        275                 280                 285

Lys Val Tyr Ala Glu Glu Ile Thr Thr Ala Trp Glu Thr Gly Glu Asn
    290                 295                 300

Leu Glu Arg Val Ala Arg Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
```

```
                       325                 330                 335
Ile Gly Gln Ser Leu Trp Asp Val Ser Arg Ser Thr Gly Asn Leu
                340                 345                 350
Val Glu Trp Phe Leu Leu Arg Lys Ala Tyr Glu Arg Asn Glu Leu Ala
            355                 360                 365
Pro Asn Lys Pro Asp Glu Lys Glu Leu Ala Arg Arg Gln Ser Tyr
        370                 375                 380
Glu Gly Gly Tyr Val Lys Glu Pro Arg Gly Leu Trp Glu Asn Ile
385                 390                 395                 400
Val Tyr Leu Asp Phe Arg Ser Leu Tyr Pro Ser Ile Ile Thr His
                405                 410                 415
Asn Val Ser Pro Asp Thr Leu Asn Arg Glu Gly Cys Lys Glu Tyr Asp
            420                 425                 430
Val Ala Pro Gln Val Gly His Arg Phe Cys Lys Asp Phe Pro Gly Phe
        435                 440                 445
Ile Pro Ser Leu Leu Gly Asp Leu Leu Glu Glu Arg Gln Lys Ile Lys
    450                 455                 460
Lys Lys Met Lys Ala Thr Ile Asp Pro Ile Glu Arg Lys Leu Leu Asp
465                 470                 475                 480
Tyr Arg Gln Arg Ala Ile Lys Ile Leu Ala Asn Ser Tyr Tyr Gly Tyr
                485                 490                 495
Tyr Gly Tyr Ala Arg Ala Arg Trp Tyr Cys Lys Glu Cys Ala Glu Ser
            500                 505                 510
Val Thr Ala Trp Gly Arg Glu Tyr Ile Thr Met Thr Ile Lys Glu Ile
        515                 520                 525
Glu Glu Lys Tyr Gly Phe Lys Val Ile Tyr Ser Asp Thr Asp Gly Phe
    530                 535                 540
Phe Ala Thr Ile Pro Gly Ala Asp Ala Glu Thr Val Lys Lys Lys Ala
545                 550                 555                 560
Met Glu Phe Leu Lys Tyr Ile Asn Ala Lys Leu Pro Gly Ala Leu Glu
                565                 570                 575
Leu Glu Tyr Glu Gly Phe Tyr Lys Arg Gly Phe Phe Val Thr Lys Lys
            580                 585                 590
Lys Tyr Ala Val Ile Asp Glu Glu Gly Lys Ile Thr Thr Arg Gly Leu
        595                 600                 605
Glu Ile Val Arg Arg Asp Trp Ser Glu Ile Ala Lys Glu Thr Gln Ala
    610                 615                 620
Arg Val Leu Glu Ala Leu Leu Lys Asp Gly Asp Val Glu Lys Ala Val
625                 630                 635                 640
Arg Ile Val Lys Glu Val Thr Glu Lys Leu Ser Lys Tyr Glu Val Pro
                645                 650                 655
Pro Glu Lys Leu Val Ile His Glu Gln Ile Thr Arg Asp Leu Lys Asp
            660                 665                 670
Tyr Lys Ala Thr Gly Pro His Val Ala Val Ala Lys Arg Leu Ala Ala
        675                 680                 685
Arg Gly Val Lys Ile Arg Pro Gly Thr Val Ile Ser Tyr Ile Val Leu
    690                 695                 700
Lys Gly Ser Gly Arg Ile Gly Asp Arg Ala Ile Pro Phe Asp Glu Phe
705                 710                 715                 720
Asp Pro Thr Lys His Lys Tyr Asp Ala Glu Tyr Tyr Ile Glu Asn Gln
                725                 730                 735
Val Leu Pro Ala Val Glu Arg Ile Leu Arg Ala Phe Gly Tyr Arg Lys
            740                 745                 750
```

Glu Asp Leu Arg Tyr Gln Lys Thr Arg Gln Val Gly Leu Ser Ala Trp
            755                 760                 765

Leu Lys Pro Lys Gly Thr
    770

<210> SEQ ID NO 16
<211> LENGTH: 775
<212> TYPE: PRT
<213> ORGANISM: Pyrococcus furiosus

<400> SEQUENCE: 16

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Asp Ile Glu Thr
130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu

```
                        340                 345                 350
Val Glu Trp Phe Leu Leu Arg Lys Ala Tyr Glu Arg Asn Glu Val Ala
            355                 360                 365

Pro Asn Lys Pro Ser Glu Glu Glu Tyr Gln Arg Arg Leu Arg Glu Ser
370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
            435                 440                 445

Phe Ile Pro Ser Leu Leu Gly His Leu Leu Glu Glu Arg Gln Lys Ile
            450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
            515                 520                 525

Leu Glu Glu Lys Phe Gly Phe Lys Val Leu Tyr Ile Asp Thr Asp Gly
            530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
            595                 600                 605

Leu Glu Ile Val Arg Arg Asp Trp Ser Glu Ile Ala Lys Glu Thr Gln
            610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
            675                 680                 685

Ala Lys Gly Val Lys Ile Lys Pro Gly Met Val Ile Gly Tyr Ile Val
            690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
            755                 760                 765
```

Trp Leu Asn Ile Lys Lys Ser
    770               775

<210> SEQ ID NO 17
<211> LENGTH: 774
<212> TYPE: PRT
<213> ORGANISM: Thermococcus litoralis

<400> SEQUENCE: 17

Met Ile Leu Asp Thr Asp Tyr Ile Thr Lys Asp Gly Lys Pro Ile Ile
1               5                   10               15

Arg Ile Phe Lys Lys Glu Asn Gly Glu Phe Lys Ile Glu Leu Asp Pro
          20               25               30

His Phe Gln Pro Tyr Ile Tyr Ala Leu Leu Lys Asp Asp Ser Ala Ile
              35              40             45

Glu Glu Ile Lys Ala Ile Lys Gly Glu Arg His Gly Lys Thr Val Arg
  50               55                 60

Val Leu Asp Ala Val Lys Val Arg Lys Lys Phe Leu Gly Arg Glu Val
65               70                75               80

Glu Val Trp Lys Leu Ile Phe Glu His Pro Gln Asp Val Pro Ala Met
              85              90             95

Arg Gly Lys Ile Arg Glu His Pro Ala Val Val Asp Ile Tyr Glu Tyr
         100               105             110

Asp Ile Pro Phe Ala Lys Arg Tyr Leu Ile Asp Lys Gly Leu Ile Pro
        115              120             125

Met Glu Gly Asp Glu Glu Leu Lys Leu Leu Ala Phe Asp Ile Glu Thr
    130               135               140

Phe Tyr His Glu Gly Asp Glu Phe Gly Lys Gly Glu Ile Ile Met Ile
145               150              155           160

Ser Tyr Ala Asp Glu Glu Glu Ala Arg Val Ile Thr Trp Lys Asn Ile
              165              170             175

Asp Leu Pro Tyr Val Asp Val Val Ser Asn Glu Arg Glu Met Ile Lys
        180              185             190

Arg Phe Val Gln Val Val Lys Glu Lys Asp Pro Asp Val Ile Ile Thr
     195               200             205

Tyr Asn Gly Asp Asn Phe Asp Leu Pro Tyr Leu Ile Lys Arg Ala Glu
    210               215               220

Lys Leu Gly Val Arg Leu Val Leu Gly Arg Asp Lys Glu His Pro Glu
225               230              235           240

Pro Lys Ile Gln Arg Met Gly Asp Ser Phe Ala Val Glu Ile Lys Gly
             245              250             255

Arg Ile His Phe Asp Leu Phe Pro Val Val Arg Arg Thr Ile Asn Leu
        260              265             270

Pro Thr Tyr Thr Leu Glu Ala Val Tyr Glu Ala Val Leu Gly Lys Thr
    275               280               285

Lys Ser Lys Leu Gly Ala Glu Glu Ile Ala Ala Ile Trp Glu Thr Glu
    290               295               300

Glu Ser Met Lys Lys Leu Ala Gln Tyr Ser Met Glu Asp Ala Arg Ala
305               310              315           320

Thr Tyr Glu Leu Gly Lys Glu Phe Phe Pro Met Glu Ala Glu Leu Ala
             325              330             335

Lys Leu Ile Gly Gln Ser Val Trp Asp Val Ser Arg Ser Ser Thr Gly
        340              345             350

Asn Leu Val Glu Trp Tyr Leu Leu Arg Val Ala Tyr Ala Arg Asn Glu
     355               360             365

```
Leu Ala Pro Asn Lys Pro Asp Glu Glu Tyr Lys Arg Arg Leu Arg
    370                 375                 380

Thr Thr Tyr Leu Gly Gly Tyr Val Lys Glu Pro Glu Lys Gly Leu Trp
385                 390                 395                 400

Glu Asn Ile Ile Tyr Leu Asp Phe Arg Ser Leu Tyr Pro Ser Ile Ile
                405                 410                 415

Val Thr His Asn Val Ser Pro Asp Thr Leu Glu Lys Glu Gly Cys Lys
            420                 425                 430

Asn Tyr Asp Val Ala Pro Ile Val Gly Tyr Arg Phe Cys Lys Asp Phe
        435                 440                 445

Pro Gly Phe Ile Pro Ser Ile Leu Gly Asp Leu Ile Ala Met Arg Gln
    450                 455                 460

Asp Ile Lys Lys Lys Met Lys Ser Thr Ile Asp Pro Ile Glu Lys Lys
465                 470                 475                 480

Met Leu Asp Tyr Arg Gln Arg Ala Ile Lys Leu Leu Ala Asn Ser Tyr
                485                 490                 495

Tyr Gly Tyr Met Gly Tyr Pro Lys Ala Arg Trp Tyr Ser Lys Glu Cys
            500                 505                 510

Ala Glu Ser Val Thr Ala Trp Gly Arg His Tyr Ile Glu Met Thr Ile
        515                 520                 525

Arg Glu Ile Glu Glu Lys Phe Gly Phe Lys Val Leu Tyr Ala Asp Thr
    530                 535                 540

Asp Gly Phe Tyr Ala Thr Ile Pro Gly Glu Lys Pro Glu Leu Ile Lys
545                 550                 555                 560

Lys Lys Ala Lys Glu Phe Leu Asn Tyr Ile Asn Ser Lys Leu Pro Gly
                565                 570                 575

Leu Leu Glu Leu Glu Tyr Glu Gly Phe Tyr Leu Arg Gly Phe Phe Val
            580                 585                 590

Thr Lys Lys Arg Tyr Ala Val Ile Asp Glu Glu Gly Arg Ile Thr Thr
        595                 600                 605

Arg Gly Leu Glu Val Val Arg Arg Asp Trp Ser Glu Ile Ala Lys Glu
    610                 615                 620

Thr Gln Ala Lys Val Leu Glu Ala Ile Leu Lys Glu Gly Ser Val Glu
625                 630                 635                 640

Lys Ala Val Glu Val Val Arg Asp Val Val Glu Lys Ile Ala Lys Tyr
                645                 650                 655

Arg Val Pro Leu Glu Lys Leu Val Ile His Glu Gln Ile Thr Arg Asp
            660                 665                 670

Leu Lys Asp Tyr Lys Ala Ile Gly Pro His Val Ala Ile Ala Lys Arg
        675                 680                 685

Leu Ala Ala Arg Gly Ile Lys Val Lys Pro Gly Thr Ile Ile Ser Tyr
    690                 695                 700

Ile Val Leu Lys Gly Ser Gly Lys Ile Ser Asp Arg Val Ile Leu Leu
705                 710                 715                 720

Thr Glu Tyr Asp Pro Arg Lys His Lys Tyr Asp Pro Asp Tyr Tyr Ile
                725                 730                 735

Glu Asn Gln Val Leu Pro Ala Val Leu Arg Ile Leu Glu Ala Phe Gly
            740                 745                 750

Tyr Arg Lys Glu Asp Leu Arg Tyr Gln Ser Ser Lys Gln Thr Gly Leu
        755                 760                 765

Asp Ala Trp Leu Lys Arg
    770
```

DNA POLYMERASES FROM THE RED SEA BRINE POOL

PRIORITY CLAIM

This application claims priority to International Application No. PCT/IB2015/001423, filed Apr. 10, 2015, which claims priority to U.S. Provisional Application No. 61/978,406, filed Apr. 11, 2014, which is incorporated by reference in its entirety.

SEQUENCE LISTING

The instant application contains a Sequence Listing which has been submitted electronically in ASCII format and is hereby incorporated by reference in its entirety. Said ASCII copy, created on Oct. 14, 2015, is named 18605.0094PCT_SL.txt and is 53,211 bytes in size.

FIELD OF THE INVENTION

The present invention relates to DNA polymerases.

BACKGROUND

Polymerase chain reaction (PCR) is a method for the rapid and exponential amplification of target nucleic acid sequences. It has found numerous applications in gene characterization and molecular cloning technologies including the direct sequencing of PCR amplified DNA, the determination of allelic variation, and the detection of infectious and genetic disease disorders. Various thermostable DNA polymerases have been used for PCR applications; for example, Taq polymerase isolated from *Therms aquaticus* (Taq), pfu polymerase derived from *Pyrococcus furiosus*, KOD polymerase isolated from *Thermococcus kodakaraensis*, and Vent™ DNA polymerase isolated from *Thermococcus litoralis* (Tli). See, for example, U.S. Pat. Nos. 6,008,025, 5,545,552 and 5,489,523, each of which is incorporated by reference in its entirety.

SUMMARY

In one aspect, a DNA polymerase composition for amplifying nucleic acids includes an isolated DNA polymerase having an amino acid residue having at least 80% homology with the sequence of SEQ ID NOS:1-4. The polymerase can be isolated from a brine pool thermophilic archaea species. The polymerase can have about 40% sequence homology to DNA polymerase isolated from *Thermococcus litoralis*.

In certain embodiments, the polymerase retains at least 100% of its optimal DNA polymerase activity in the presence of chloride ion at a concentration as high as 300 mM. The activity increased with increasing the chloride ion concentration with 300 mM being the optimal concentration.

In certain embodiments, the polymerase retains at least 50% of its optimal DNA polymerase activity in the presence of sulfate ion at a concentration as high as 300 mM. The activity increases with increasing the sulfate ion concentration with 100 mM being the optimal concentration and decrease to 50% at sulfate concentration of 300 mM.

In certain embodiments, the polymerase retains 100% of its optimal DNA polymerase activity in the presence of K-glutamate at a concentration as high as 250 mM. The activity increases with increasing the K-glutamate concentration with 250 mM being the optimal concentration.

In certain embodiments, the polymerase retains at least 50% of its optimal DNA polymerase activity in the presence of $Zn^{2+}$ ion at a concentration as high as 1 mM. The activity is optimal at 0.5 mM $Zn^{2+}$ ion concentration and decrease to 50% at 1 mM.

In certain embodiments, the polymerase retains 100% of its DNA polymerase activity in the presence of $Mg^{2+}$ ion at a concentration as high as 100 mM. The activity increases with increasing the $Mg^{2+}$ ion concentration with 100 mM being the optimal concentration.

In certain embodiments, the polymerase has a DNA extension rate of greater than 450 bases per second.

In certain embodiments, the polymerase has a DNA extension processivity of an average of 2000 bases per one cycle of DNA binding event.

In certain embodiments, the polymerase has a DNA proofreading activity that is at least 2 fold more active than pfu polymerase.

In certain embodiments, the polymerase retains its stability 100% after being heated at 65° C. for 15 minutes.

In certain embodiments, the polymerase is active at room temperature.

In certain embodiments, the polymerase retains 100% of its DNA polymerase activity in pH conditions between 7.5-9.0.

In another aspect, a method for amplifying nucleic acid can include reacting DNA as a template, a primer, dNTP and the DNA polymerase composition, and extending the primer to synthesize a DNA primer extension product.

In other aspect, a method for amplifying nucleic acid where the ability of the polymerase to extend DNA under high salt and metal ion concentration and different type of metal ions, enables its utilization to improve currently available molecular biology, biochemical and biophysical techniques.

In another aspect, a kit for amplifying nucleic acid can include the DNA polymerase composition.

In another aspect, vector can include a gene encoding the DNA polymerase.

In another aspect, a plasmid can include a gene encoding for a recombinant form of the DNA polymerase.

Other aspects, embodiments, and features will be apparent from the following description, the drawings, and the claims.

4B is an image of KOD polymerase activities in the presence of different Mg2+ concentrations.

Figure 5:
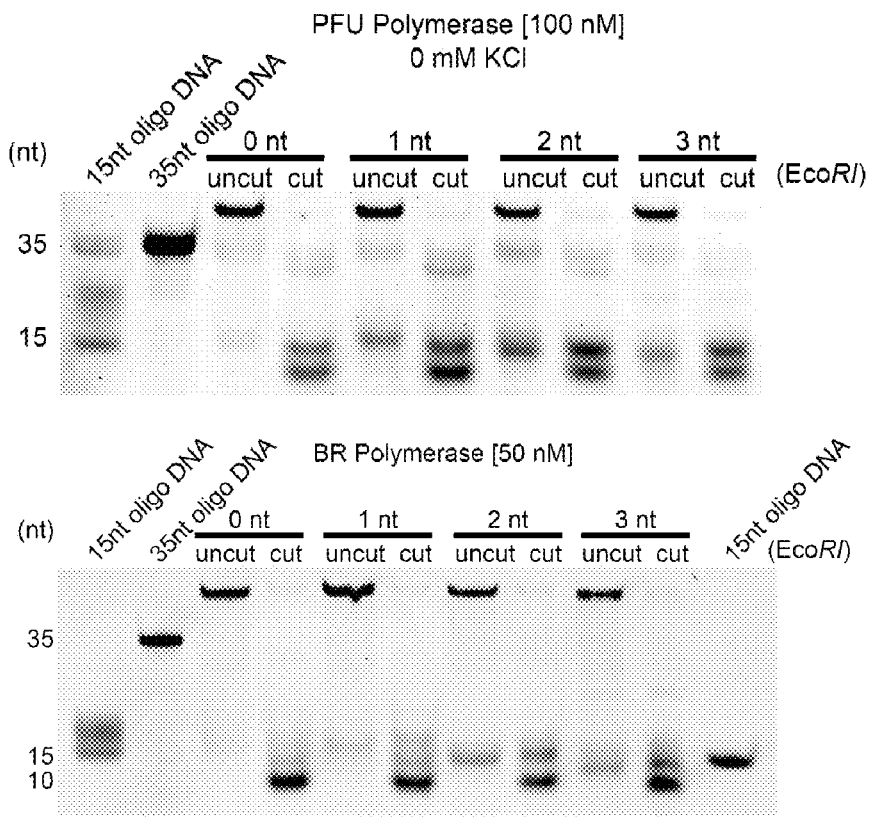

FIG. 5 is an image comparing BR3 polymerase and pfu polymerase proofreading activities. FIG. 5 discloses SEQ ID NOS 7-11, respectively, in order of appearance.

Figure 6:
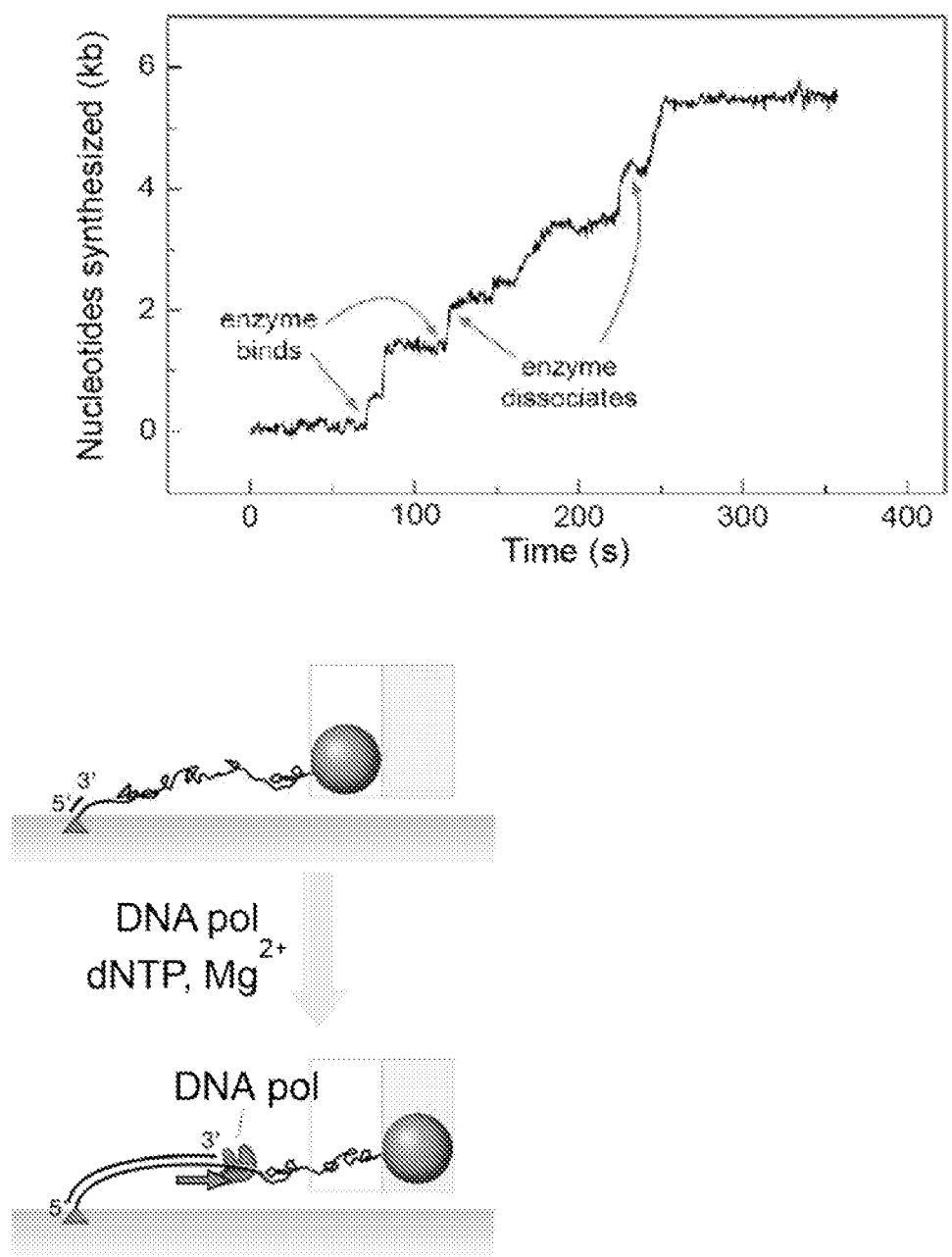

FIG. 6 is an image and a graph depicting the single molecule assay used to measure rate and processivity of BR3 and pfu polymerases and the histograms of rate and processivity of DNA synthesis by BR3 and pfu polymerases.

Figure 7:
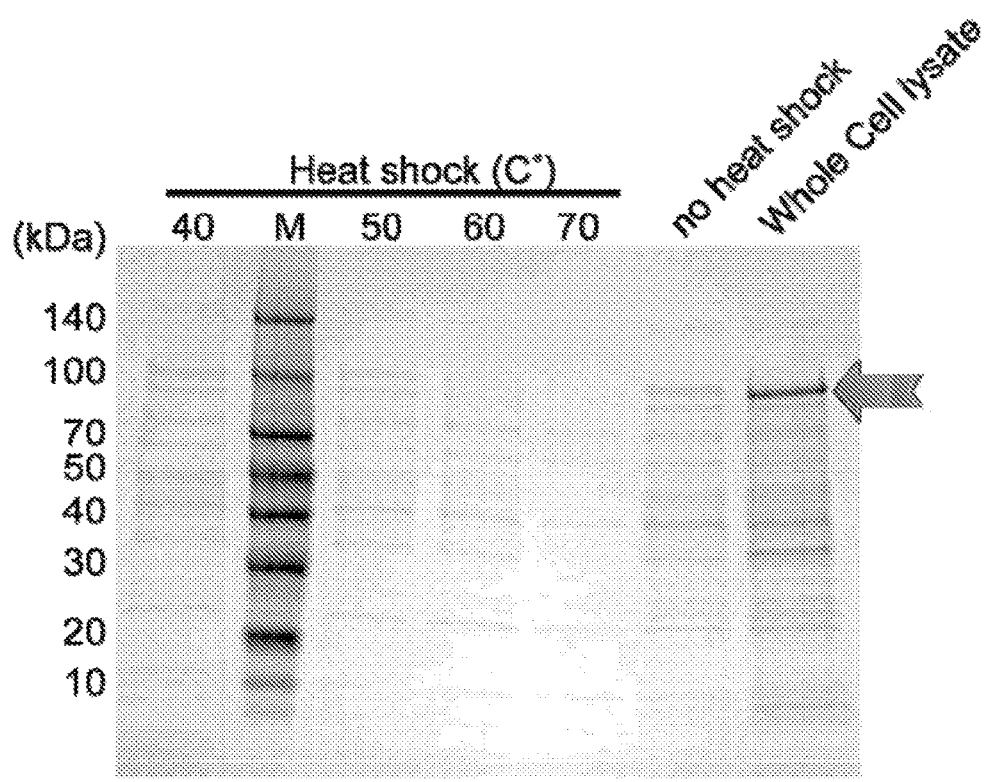

FIG. 7 is an image depicting the thermal stability of BR3 polymerase.

Figure 8:
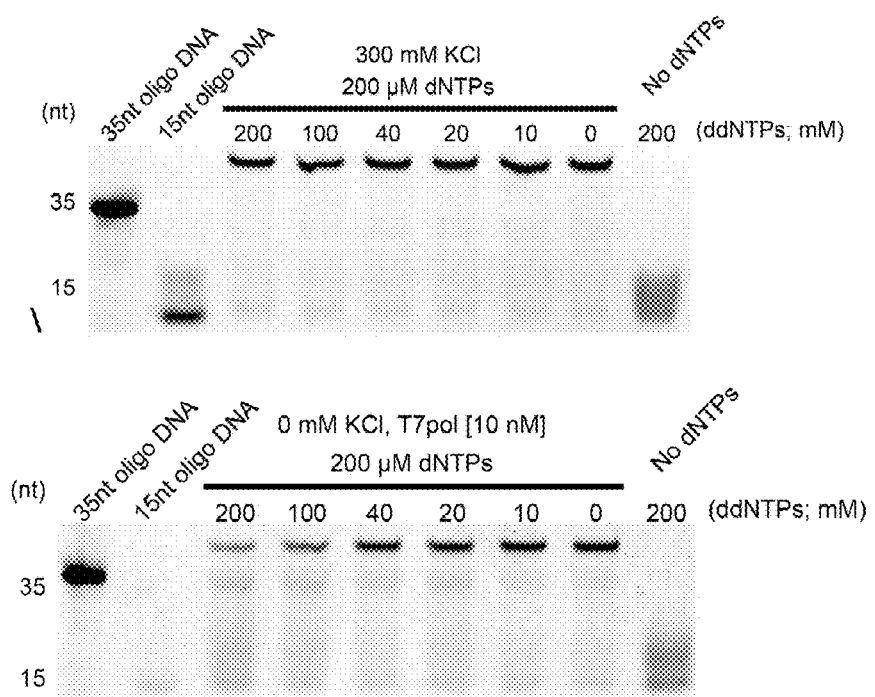
Figure 8:
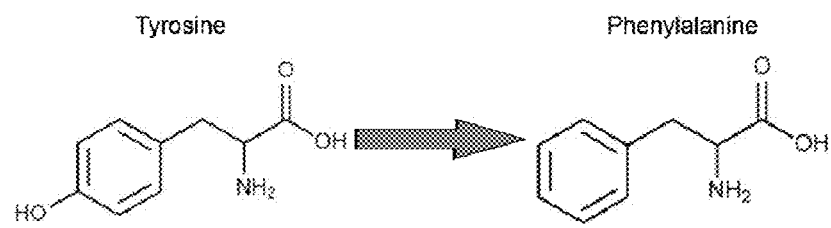

FIG. 8 is an image depicting the ddNTP incorporation efficiency of BR3 polymerase and the strategy to engineer its active site to incorporate ddNTP. FIG. 8 discloses SEQ ID NOS 12 and 13, respectively, in order of appearance.

FIG. 9 represents the sequences of BR1, BR2, BR3, and BR6 polymerases.

FIG. 10 represents the open reading frame sequence of the BR3 polymerase (Nucleotide sequence disclosed as SEQ ID NO: 14, amino acid sequence disclosed as SEQ ID NO:3).

FIG. 11 represents primary sequence alignment of BR3 (SEQ ID NO: 3), KOD (SEQ ID NO: 15), Pfu (SEQ ID NO: 16) and Tli (SEQ ID NO: 17) polymerases. Sequences are color-highlighted based on common domain structures in DNA polymerases, key amino acids involved in catalysis are in bold red and blue and cysteine residues involved in thermal stability of the polymerase structure are in bold yellow.

DETAILED DESCRIPTION

The deep-sea anoxic brines of the Red Sea are considered to be one of the most remote, challenging and extreme environments on Earth, while remaining one of the least studied. Approximately 25 such brine-filled pools are currently known, with all of them being anoxic, highly saline deep-sea water bodies with elevated temperatures, heavy metal concentration with different types of metal ions that form characteristically sharp gradient-rich interfaces with the overlaying sea water. See Backer H & Schoell M (1972) New deeps with brines and metalliferous sediments in Red Sea. *Nature-Physical Science* 240(103):153, and Hartmann M, Scholten J C, Stoffers P, & Wehner F (1998) Hydrographic structure of brine-filled deeps in the Red Sea—new results from the Shaban, Kebrit, Atlantis II, and Discovery Deep. *Mar Geol* 144(4):311-330, each of which is incorporated by reference in its entirety. In contrast to frequent geological and geochemical studies, very few studies have focused on the microbiology of the deep-sea brines of the Red Sea, and none have concentrated on their biotechnological applications. Initial cultivation-independent and cultivation-based studies have provided a first glimpse on the unexpected enormous biodiversity of the local microbial communities, with identification of several new groups and the isolation of new extremophilic microorganisms that thrive in these environments. See Antunes A, Eder W, Fareleira P, Santos H, & Huber R (2003) Salinisphaera shabanensis gen. nov., sp nov., a novel, moderately halophilic bacterium from the brine-seawater interface of the Shaban Deep, Red Sea. *Extremophiles* 7(1):29-34, Antunes A, et al. (2008) A new lineage of halophilic, wall-less, contractile bacteria from a brine-filled deep of the Red Sea. *J Bacteriol* 190(10):3580-3587, Antunes A, et al. (2008) Halorhabdus tiamatea sp nov., a non-pigmented, extremely halophilic archaeon from a deep-sea, hypersaline anoxic basin of the Red Sea, and emended description of the genus Halorhabdus. *Int J Syst Evol Micr* 58:215-220, Eder W, Ludwig W, & Huber R (1999) Novel 16S rRNA gene sequences retrieved from highly saline brine sediments of Kebrit Deep, Red Sea. *Arch Microbiol* 172(4):213-218, Eder W, Jahnke L L, Schmidt M, & Huber R (2001) Microbial diversity of the brine-seawater interface of the Kebrit Deep, Red Sea, studied via 16S rRNA gene sequences and cultivation methods. *Appl Environ Microb* 67(7):3077-3085, and Eder W, Schmidt M, Koch M, Garbe-Schonberg D, & Huber R (2002) Prokaryotic phylogenetic diversity and corresponding geochemical data of the brine-seawater interface of the Shaban Deep, Red Sea. *Environ Microbiol* 4(11):758-763, each of which is incorporated by reference in its entirety. Because of the unusually harsh conditions of this environment, it is highly likely that the residing microbes developed novel metabolic pathways, transport systems across their membranes, enzymes, and chemicals in order to survive.

This environment presents the harshest conditions for the DNA replication machinery as well as DNA processing enzymes to copy and to maintain the genomic DNA, indicating the utilization of novel adaptive mechanisms and nucleic acid binding proteins. Archaeal and bacterial species from the brine pool can be used to screen for novel DNA sequencing polymerase and other key DNA modifying enzymes.

The classical chain-termination method used for DNA sequencing, the Sanger method, relies on using a DNA polymerase that has high rate of incorporation of the chain terminator dideoxynucleoside triphosphate (ddNTP). See Tabor S & Richardson C C (1995) A single residue in DNA polymerases of the *Escherichia coli* DNA polymerase I family is critical for distinguishing between deoxy- and dideoxyribonucleotides. *Proc Natl Acad Sci USA* 92(14):6339-6343, which is incorporated by reference in its entirety. DNA polymerases normally catalyze a nucleophilic attack of the 3'-OH group of the primer on the α-phosphate of the incoming dNTP. Two $Mg^{2+}$ ions are required in this reaction to align the primer/template strand and the incoming dNTP and to mediate the substitution nucleophilic attack reaction. See Johnson A & O'Donnell M (2005) Cellular DNA replicases: components and dynamics at the replication fork. *Annu Rev Biochem* 74:283-315, and Hamdan S M & Richardson C C (2009) Motors, switches, and contacts in the replisome, each of which is incorporated by reference in its entirety. The lack of the 3'-OH nuleophilic group in the ddNTP is the reason for its action as a DNA polymerase inhibitor. See Tabor S & Richardson C C (1995) A single residue in DNA polymerases of the *Escherichia coli* DNA polymerase I family is critical for distinguishing between deoxy- and dideoxyribonucleotides. *Proc Natl Acad Sci USA* 92(14):6339-6343, which is incorporated by reference in its entirety. During sequencing, DNA synthesis reaction starts from a specific primer and ends upon the incorporation of ddNTP. By using either dye- or radiolabel-based ddNTP, the identity of these products can be mapped. In general, DNA polymerases polymerize the dNTP with very high accuracy (1 mistake per $10^3$-$10^5$ incorporated nucleotides) and encode for a proofreading exonucleases activity to remove miscorporated nucleotide (accuracy increased to 1 mistake per $10^5$-$10^7$ incorporated nucleotides). Therefore, the ideal DNA sequencing polymerase will have high rate and high processivity of DNA synthesis, high accuracy of dNTP incorporation, proofreading exonuclease activity, high thermal stability and high rate of incorporation of ddNTP. Indeed all these properties have been fulfilled with the introduction of four DNA polymerases to the market that are isolated from archaea species, *Pyrococcus furiosus* DNA polymerase (pfu DNA Pol), *Thermococcus litoralis* Vent™ DNA polymerase (Vent DNA Pol), *Thermococcus Kodakarensis* (KOD Pol) and *Therms Aquaticus* DNA polymerase (Taq Pol) (Table 1).

TABLE 1

Characteristics of DNA Polymerases. The table is adopted from Takagi M et al. (1997) Characterization of DNA polymerase from *Pyrococcus* sp. strain KOD1 and its application to PCR. Applied and Environmental Microbilogy 63(11): 4504-4510

|  | KOD | PFU | Taq |
|---|---|---|---|
| Species | *Thermococcus kodakaraensis* | *Pyrococcus furiosus* | *Thermus aquaticus* YT-1 |
| Fidelity | 0.0035 | 0.0039 | 0.013 |
| Elongation rate (bases/second) | 106-138 | 25 | 61 |
| Processivity (nucleotide bases) | >300 | <20 | unavailable |

Disclosed herein is a method of utilizing DNA polymerases from the Brine pool with the aim of generating a commercial polymerase that has the robust reaction features of utilizing wide range of salt and metal ion concentration and metal ion types as well as enhanced rate processivity and proofreading activity. Also disclosed is a method and a composition for amplifying nucleic acid where the ability of the polymerase to extend DNA under high salt and high metal ion concentrations, in the presence of different type of metal ions, and high temperature conditions enables its utilization to improve currently available molecular biology, biochemical and biophysical techniques. None of the conventional polymerases are ideal for the harsh conditions like high salt concentrations, high metal concentrations, and high temperature, let alone combinations of two or more of these conditions. Disclosed herein is a polymerase that can not only tolerate under one of these harsh conditions, but also can tolerate various combinations of those conditions, e.g. high salt and metal concentrations, high metal concentration and high temperate, high salt concentration and high temperate, or high salt and metal concentrations and high temperate.

Robust DNA sequencing enzymes isolated from the Brine pool can sustain wide range of salt and metal ion concentrations, different type of metal ions and wide range of pH during PCR. Four clones of DNA polymerase have been identified from the brine pool (FIG. 9, Table 2). These polymerases from microorganisms from the Brine pool can be used for conducting a PCR reaction at wide range of buffer conditions and metal ions concentration and types. Optimization of PCR remains tricky as it might require screening for the appropriate salt and metal ion concentrations that lead to high yield, high processivity and accuracy of the amplified DNA fragment. The ability of thermal archaea species from the brine pool to replicate their genome at high salt concentration indicates that their DNA polymerases binds to the DNA with relatively high affinity, which could potentially enhance the sensitivity of the PCR, and could therefore tolerate wide range of salt concentrations. Furthermore, the ability of these DNA polymerases to tolerate high metal ion concentrations indicates that they can work at wide range of metal ion concentrations. Finally, the ability of these DNA polymerases to tolerate different type of metal ions indicates that they can work at wide range of metal ion types. DNA polymerases from the brine pool thermophilic archaea species were cloned, expressed, purified and characterized.

TABLE 2

Identification of DNA Polymerases from the Brine Pool.

| | size | Homologous species | Enzyme | % homology |
|---|---|---|---|---|
| Clone 1 (SEQ ID NO: 1) | 2100bp, 700aa | *Candidatus Nitrososphaera gargensis* | DNA Polymerase B | 25% |
| Clone 2 (SEQ ID NO: 2) | 2352bp, 784aa | *Thermococcus celer* | DNA dependent Polymerase | 42% |
| Clone 3 (SEQ ID NO: 3) | 2457bp, 819aa | *Thermococcus litoralis* | DNA dependent Polymerase | 42% |
| Clone 6 (SEQ ID NO: 4) | 2400bp, 800aa | *Candidatus Nanosalinarum* | DNA dependent Polymerase | 42% |

Especially, Clone 3 (termed BR3, FIG. 10) which is 42% homologous to DNA dependent polymerase of *Thermococcus litoralis* shows much more robust properties than any known commercially available DNA polymerases that are used in PCR and DNA sequencing.

Figure 1A:
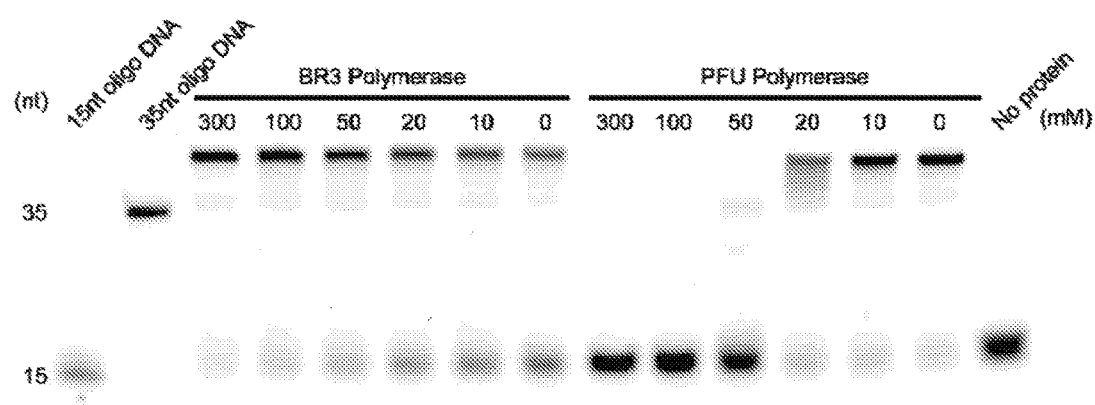
FIG. 1A is an image comparing BR3 polymerase and pfu polymerase activities at different salt concentrations. Salt used in these experiments is NaCl. BR3 and pfu concentrations are 50 nM.
Figure 1B:
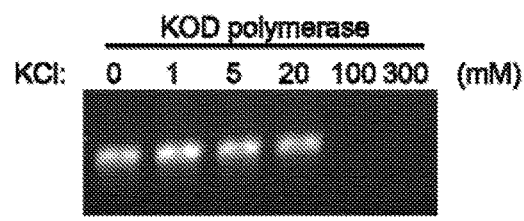
FIG. 1B is an image of KOD polymerase activities at different salt concentrations. Salt used in this experiment is KCl and KOD concentration is 50 nM.
Figure 2A:
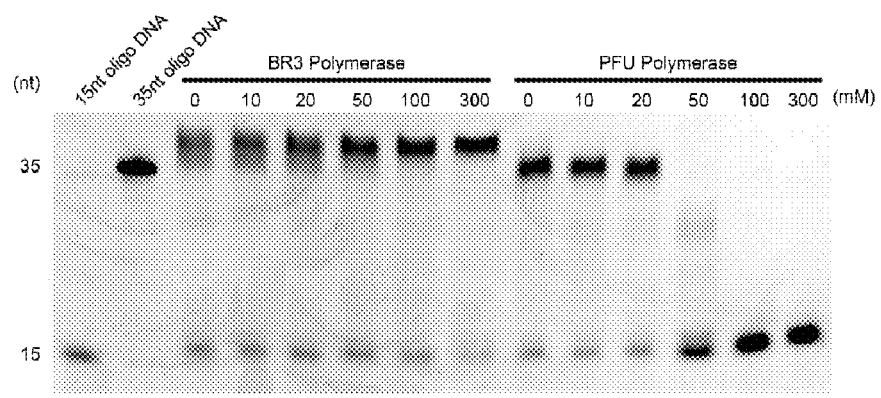
FIGS. 2A-2C are images comparing BR3 polymerase and pfu polymerase activities in the presence of different salts. Salts used in these experiments are: KCl (2A), $NH_4(SO)_4$ (B) and K-Glutamate (C). BR3 and pfu concentrations are 50 nM.
Figure 2B:
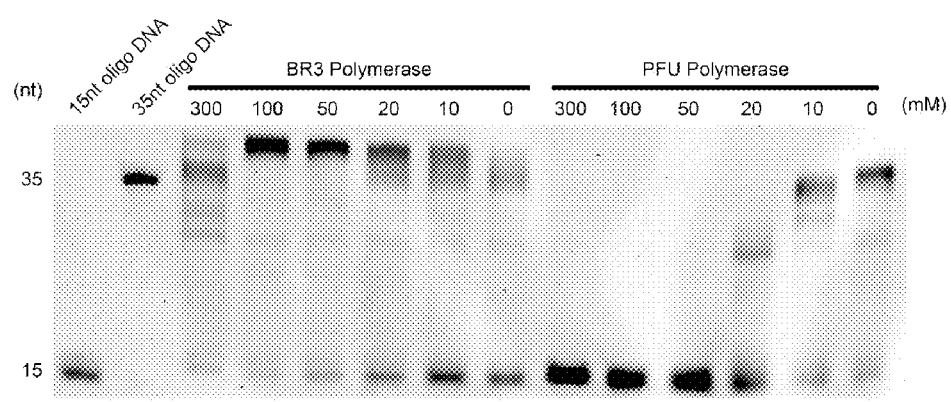
Figure 2C:
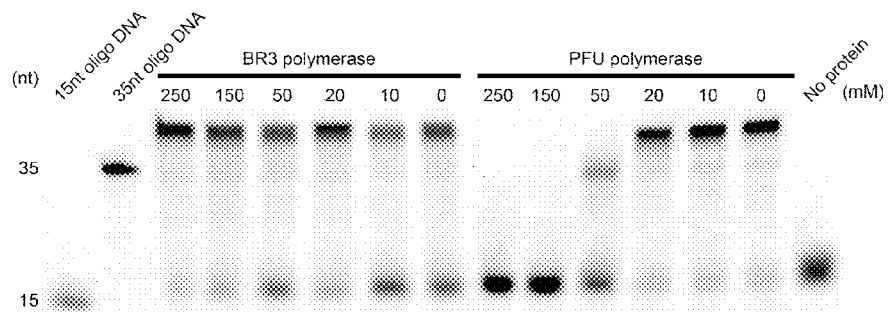

BR3 tolerates extremely versatile buffer conditions. FIGS. 1A and 1B show that BR3 polymerase retains its optimal activity up to 300 mM NaCl whereas pfu and KOD polymerases retains their optimal activity only up to 10 mM. BR3 polymerase also tolerates different types of salts. FIG. 2 shows that BR3 polymerase tolerates up to 300 mM KCl (FIG. 2A), up to 100 mM $(NH_4)_2SO_4$ (FIG. 2B), and up to 250 mM K-Glutamate (FIG. 2C). The range is at least 15-30 fold higher than pfu polymerase.

Figure 3A:
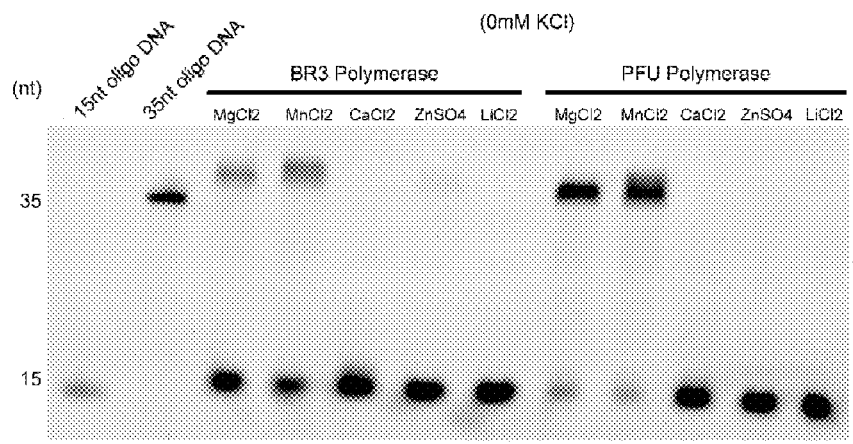
FIGS. 3A-3C are images comparing BR3 polymerase and pfu polymerase activities in the presence of different metal ions. Concentrations of metal ions used in (A) and (B) is 1 mM for $MgCl2$, $MnCl_2$, $CaCl_2$, $ZnSO_4$, LiCl. BR3 and pfu concentrations are 50 nM.
Figure 3B:
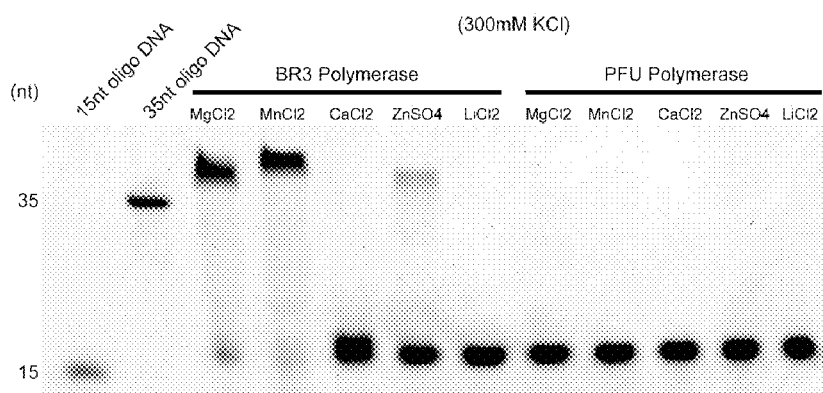
Figure 3C:
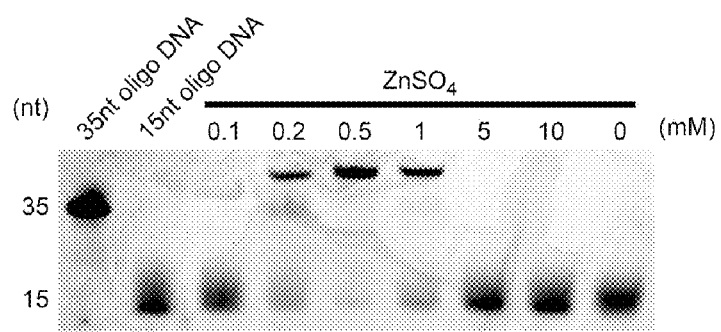
Figure 4A:
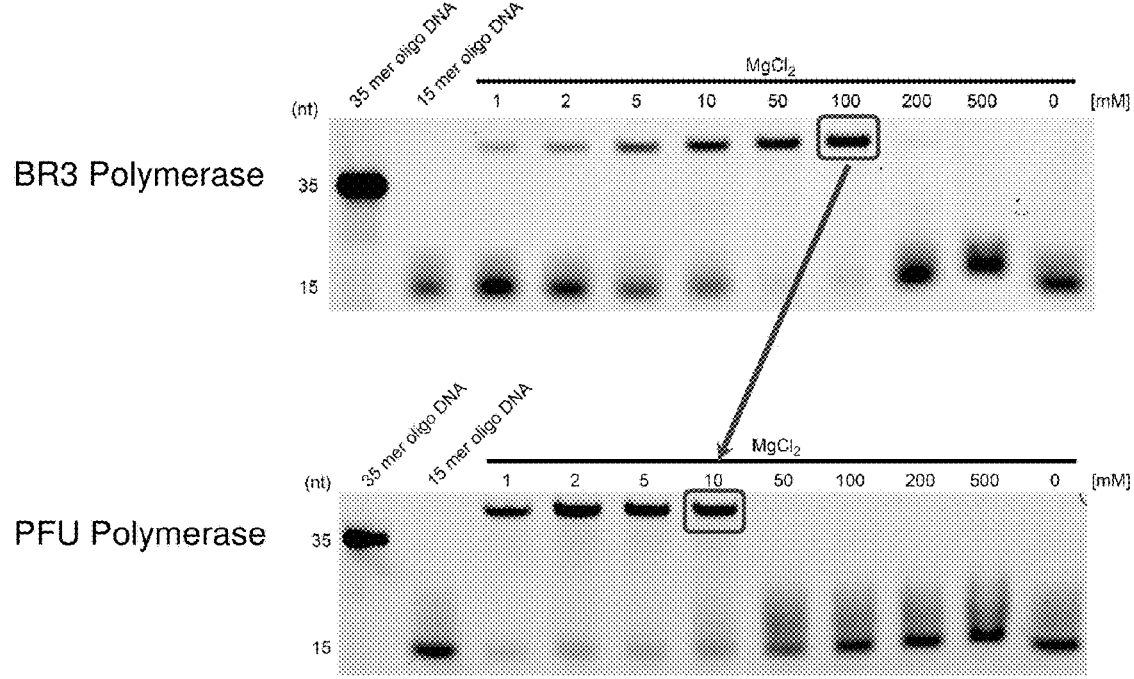
FIG. 4A is an image comparing BR3 polymerase and pfu polymerase activities in the presence of different $Mg^{2+}$ concentrations. BR3 and pfu concentrations are 50 nM. FIG.
Figure 4B:
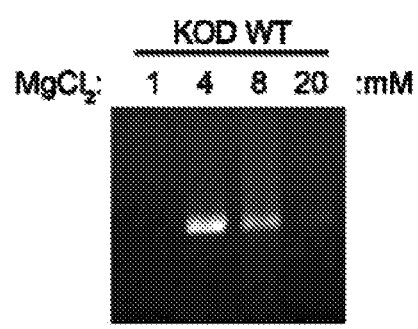

FIG. 3 shows that BR3 polymerase shows much higher activity than pfu polymerase in the presence of $MgCl_2$ and $MnCl_2$ when the salt concentration is high (FIG. 3B). Moreover, BR3 polymerase shows high metal ion resistance, for example 0.1-100 mM $MgCl_2$ (FIGS. 4A and 4B). This range is 10-fold higher than pfu polymerase and KOD polymerase. When the salt concentration is low (FIG. 3A), pfu polymerase shows higher activity in the presence of $MgCl_2$ and $MnCl_2$. Neither polymerases show a significant activity when calcium or lithium ions are present. It is notable that in the high salt concentration, BR3 polymerase retains activity in the presence of zinc ions (FIGS. 3B and 3C). BR3 polymerase is the first known polymerase to use zinc ions or any metal ions other than $Mg^{2+}$ and $Mn^{2+}$.

BR3 polymerase has at least 2-fold higher proofreading activity than pfu polymerase (FIG. 5). FIG. 5 shows that BR3 polymerase only requires half the concentration of pfu polymerase to produce the same activity level in the presence of up to three mismatches on the primer strand.

FIG. 6 shows the single molecule assay that was used to measure the rate and processivity of BR3 and compare it with pfu polymerase and Table 3 shows the results from this measurement, where BR3 polymerase displays at least 1.5-fold higher rate and processivity than pfu polymerase.

TABLE 3

Comparison of rate and processivity of BR3 polymerase and pfu polymerase

| | Rate (base/sec) | Processivity (kb) |
|---|---|---|
| BR3 polymerase | 463.34 ± 34.73 | 2.0 ± 0.3 |
| PFU polymerase | 305.5 ± 40.46 | 1.3 ± 0.1 |

BR3 polymerase retains the same polymerization activity at pH range between 7.5-9.0. It also showed high thermal stability up to 65° C. (FIG. 7). Its thermal stability can be likely increased by inducing the formation of a highly conserved disulfide bond in the active site of extreme thermophilic polymerases. BR3 polymerase also discriminates well against the incorporation of ddNTP (FIG. 8). It is highly likely to increase the incorporation efficiency of ddNTP by mutating F residue in active site to Y in BR3 (FIG. 8).

These properties make this polymerase ideal to be used in DNA sequencing and molecular biology techniques with minimal reaction optimization and with different sample types and preparations.

The BR3 polymerase can be produced using recombinant techniques.

As used herein, the terms "polypeptide" and "protein" are used interchangeably to refer to a polymer of amino acid residues. The term "recombinant polypeptide" refers to a polypeptide that is produced by recombinant techniques, wherein generally DNA or RNA encoding the expressed protein is inserted into a suitable expression vector that is in turn used to transform a host cell to produce the polypeptide.

As used herein, the terms "homolog," and "homologous" refer to a polynucleotide or a polypeptide comprising a sequence that is at least about 50% identical to the corresponding polynucleotide or polypeptide sequence. Preferably homologous polynucleotides or polypeptides have polynucleotide sequences or amino acid sequences that have at least about 80%, at least about 85%, at least about 90%, at least about 91%, at least about 92%, at least about 93%, at least about 94%, at least about 95%, at least about 96%, at least about 97%, at least about 98%, or at least about 99% homology to the corresponding amino acid sequence or polynucleotide sequence. As used herein the terms sequence "homology" and sequence "identity" are used interchangeably. One of ordinary skill in the art is well aware of methods to determine homology between two or more sequences, for example, using BLAST.

A mutant or variant polypeptide refers to a polypeptide having an amino acid sequence that differs from the corresponding wild-type polypeptide by at least one amino acid. In some embodiments, the mutant polypeptide has about 1, 2, 3, 4, 5, 6, 7, 8, 9, 10, 15, 20, 30, 40, 50, 60, 70, 80, 90, 100, or more amino acid substitutions, additions, insertions, or deletions. For example, the mutant can comprise one or more conservative amino acid substitutions. As used herein, a "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine).

Preferred variants of a polypeptide or fragments a polypeptide retain some or all of the biological function (e.g., enzymatic activity) of the corresponding wild-type polypeptide. In some embodiments, the variant or fragment retains at least about 75% (e.g., at least about 80%, at least about 90%, or at least about 95%) of the biological function of the corresponding wild-type polypeptide. In other embodiments, the variant or fragment retains about 100% of the biological function of the corresponding wild-type polypeptide. In still further embodiments, the variant or fragment has greater than 100% of the biological function of the corresponding wild-type polypeptide. It is understood that the polypeptides described herein may have additional conservative or non-essential amino acid substitutions, which do not have a substantial effect on the polypeptide function.

EXAMPLES

Enzymes:

The cDNA fragment corresponding to BR3 (see FIG. 9 SEQ ID NO:3) was amplified by PCR using primers (5'-CACCATGGCAAATCAGACAACAAATGG-3' (SEQ ID NO: 5) and 5'-TTATTTGAATTTTCCGAGTTTTACTT-GTCG-3' (SEQ ID NO: 6)) and cloned into the pENTR-D/TOPO vector (Life Technology). The ORF of BR3 was transferred to pDEST17 vector (Life Technology) by using LR Clonase II enzyme mix (Life Technology). BR3 is overexpressed in *E. coli* Rozetta2 (DE3) (Novagen) after transformation with plasmids pDEST17/BR3. The overexpression was induced by addition of Isopropyl ß-D-1-thio-galactopyranoside (final concentration, 1 mM), and cells were harvested after 3 h of incubation. The collected cells were dissolved in Lysis buffer (10 mM Tris-HCl pH 8.0, 80 mM KCl, 5 mM 2-Mercaptoethanol, 1 mM EDTA) and incubated on ice with Lysozyme (final concentration, 1 mM) for 30 m, then disrupted by sonication. The crude extract was centrifuged to remove cell debris, the supernatant was collected and ammonium precipitation was performed with 80% saturation. The pellet obtained from ammonium precipitation was dissolved in Buffer A (10 mM Tris-HCl pH 8.0, 1 mM EDTA and loaded onto the Sephacryl Sepharose (GE Healthcare) column. The flow through fraction from Sephacryl Sepharose was collected and diluted enough to reduce EDTA concentration, then loaded onto HisTrap HP 5 ml (GE Healthcare) and the bound proteins were eluted by Buffer B (10 mM Tris-HCl pH 8.0, 50 mM KCl, 500 mM Imidazole). The peak fractions were collected and passed through HiTrap Heparin 1 ml (GE Healthcare) and the fractions containing pure proteins were eluted by making a gradient against Buffer C (10 mM Tris-HCl pH 8.0, 50 mM KCl, 1 M KCl). The purified BR3 proteins were dialyzed against Buffer D (50 mM Tris-HCl pH 7.5, 50 mM KCl, 1 mM DTT, 0.1% Tween20, 50% Glycerol). The protein concentration was determined by absorbance at 280 nm with the extinction coefficient and molecular weight were calculate based on the amino acid sequence of BR3 protein.

Primer Extension and Proofreading Activity Assay:

The polymerase and proofreading activities were characterized as published (see Lundberge K. S. et al. (1991) High-fidelity amplification using a thermostable DNA polymerase isolated from *Pyrococcus furiosus* (Polymerase chain reaction; mutation archaebacteria) frequency; lack; proofreading; 3'40-5 exonuclease; recombinant DNA. Gene (108): 1-6 with following modifications for the proofreading assay. The 35-mer template containing an internal EcoRI site is annealed to 15-mer Cy3-labeled primers with 0, 1, and 3 mismatch nt at the 3' terminus. Reactions were carried out at 45 C.° in 22 µl for 5 min and contained basic buffer (20 mM Tris-HCl pH 8.8, 10 mM $(NH_4)_2SO_4$, 50 mM KCl, 2 mM $MgSO_4$, 0.1% TritonX-100), 200 µM dNTPs and 1 mM $MgCl_2$. Of each reaction 10 µl was removed and reactions were stopped by adding 4 µl of stop solution (100 mM EDTA pH 8.0), the remaining 10 µl of each reaction was digested with 5 u of EcoRI at 37 C.° for 30 min. The reactions were terminated by adding 4 µl of stop solution. The synthesized product was loaded to 15% polyacrylamide/ 7.5 M urea/1× TBE denaturing gel. The gel was visualized by Typhoon TRIO (GE Healthcare). The polymerization activity of KOD was tested by conventional PCR on primed ssDNA pUC19 plasmid as a template.

Primer Extension Assay at the Single Molecule Level:

DNA synthesis was measured by monitoring the length of individual DNA molecules in real time as described previously (See Tanner, N. A. et al. (2008) Single-molecule studies of fork dynamics in *Escherichia coli* DNA replication. *Nature structural & molecular biology* (15): 170-176, Jergic, S. et al. (2013) A direct proofreader-clamp interaction stabilizes the Pol III replicase in the polymerization mode. *The EMBO journal* (32):1322-1333, and Lee, J. B. et al. (2006) DNA primase acts as a molecular brake in DNA replication. *Nature* (439):621-624, each of which is incorporated by reference in its entirety. Briefly, ssDNA template containing a biotinylated primer was attached to the surface of a glass coverslip via one end and to a magnetic bead via the other end in microfluidic flow cell (FIG. 6). The DNA molecules were stretched by a laminar flow that exerted a 2.6 piconewten (pN) drag force on the beads. Primer extension converts the surface tethered ssDNA (short) to dsDNA (long) and increase the length of the DNA as schematically illustrated in FIG. 6 and shown in the trajectories in FIG. 6. The assay was performed at 25° C. in buffer containing (20 mM Tris-HCl pH 8.8, 10 mM $(NH_4)_2SO_4$, 2 mM $MgSO_4$, 0.1% TritonX-100), 200 µM dNTPs, 1 mM $MgCl_2$, and either 250 mM KCl in case of BR3 polymerase or 50 mM KCl in case of pfu polymerase. BR3 and pfu polymerases were used at 50 nM.

Other embodiments are within the scope of the following claims.

What is claimed is:

1. A method for amplifying a polynucleotide comprising: reacting a DNA template, a primer, dNTPs and a DNA polymerase having the amino acid sequence of SEQ ID NO: 3, wherein the primer is extended in a polymerase chain reaction (PCR) to synthesize a DNA primer extension product.

2. A kit for amplifying a polynucleotide comprising a DNA polymerase having the amino acid sequence of SEQ ID NO: 3, dNTPs and a reaction buffer.

3. An expression vector for heterologous expression of a DNA polymerase, comprising a nucleic acid sequence encoding a DNA polymerase having the amino acid sequence of SEQ ID NO:3 and a heterologous promoter.

4. The expression vector of claim 3 comprising a promoter for expression in an *E. coli* host cell.

5. The expression vector of claim 3, wherein the expression vector is a plasmid.

6. The expression vector of claim 3 in a composition comprising additional polynucleotides comprising the polynucleotide sequence of SEQ ID NO: 5 and SEQ ID NO: 6.

* * * * *